(12) United States Patent
Losordo et al.

(10) Patent No.: US 9,187,540 B2
(45) Date of Patent: Nov. 17, 2015

(54) METHODS OF USING E2F2 FOR THE TREATMENT OF HYPERTENSION

(75) Inventors: Douglas W. Losordo, Chicago, IL (US); Gangjian Qin, Chicago, IL (US)

(73) Assignee: Steward Research and Specialty Projects Corporation, Boston, MA (US)

( * ) Notice: Subject to any disclaimer, the term of this patent is extended or adjusted under 35 U.S.C. 154(b) by 850 days.

(21) Appl. No.: 12/447,114

(22) PCT Filed: Oct. 29, 2007

(86) PCT No.: PCT/US2007/022804
§ 371 (c)(1),
(2), (4) Date: Jan. 20, 2010

(87) PCT Pub. No.: WO2008/057313
PCT Pub. Date: May 15, 2008

(65) Prior Publication Data
US 2010/0130414 A1    May 27, 2010

Related U.S. Application Data

(60) Provisional application No. 60/855,005, filed on Oct. 27, 2006, provisional application No. 60/855,986, filed on Oct. 31, 2006.

(51) Int. Cl.
*C07K 14/47* (2006.01)
*A61K 38/00* (2006.01)

(52) U.S. Cl.
CPC ............. *C07K 14/4705* (2013.01); *A61K 38/00* (2013.01)

(58) Field of Classification Search
None
See application file for complete search history.

(56) References Cited

U.S. PATENT DOCUMENTS 5,473,056 A    12/1995    Ivey-Hoyle et al.

OTHER PUBLICATIONS

Wells, Biochemistry, vol. 29, pp. 8509-8517, 1990.*
Zhu et al. (Molec. & Cellular Bio., vol. 21, No. 24, 2001, pp. 8547-8564).*
Ziegler et al., "Interaction of the Protein Transduction Domain of HIV-1 TAT Heparan Sulfate: Binding Mechanism and Thermodynamic Parameters", Biphysical Journal, Jan. 2004, vol. 86, No. 1, pp. 254-263.
International Search Report issued in PCT/US2007/022804, Sep. 23, 2008.

* cited by examiner

*Primary Examiner* — Hope Robinson
(74) *Attorney, Agent, or Firm* — Mintz Levin Cohn Ferris Glovsky and Popeo, P.C.; David G. Conlin; Christopher R. Cowles

(57) ABSTRACT

The present invention features compositions and methods of treating or preventing hypertension or a cardiac indication. In particular embodiments, the invention provides E2F2 as a new therapeutic target for the treatment of hypertension or a cardiac indication, and methods of increasing the expression and/or activity of E2F2.

11 Claims, 8 Drawing Sheets

SEQUENCE LISTING

```
<160> NUMBER OF SEQ ID NOS: 2

<210> SEQ ID NO 1
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Leu Gln Gly Pro Arg Ala Leu Ala Ser Ala Ala Gly Gln Thr Pro
1               5                   10                  15

Lys Val Val Pro Ala Met Ser Pro Thr Glu Leu Trp Pro Ser Gly Leu
            20                  25                  30

Ser Ser Pro Gln Leu Cys Pro Ala Thr Ala Thr Tyr Tyr Thr Pro Leu
        35                  40                  45
```

-continued

```
Tyr Pro Gln Thr Ala Pro Ala Ala Ala Pro Gly Thr Cys Leu Asp
         50                  55                  60
Ala Thr Pro His Gly Pro Glu Gly Gln Val Val Arg Cys Leu Pro Ala
 65                  70                  75                  80
Gly Arg Leu Pro Ala Lys Arg Lys Leu Asp Leu Glu Gly Ile Gly Arg
                 85                  90                  95
Pro Val Val Pro Glu Phe Pro Thr Pro Lys Gly Lys Cys Ile Arg Val
                100                 105                 110
Asp Gly Leu Pro Ser Pro Lys Thr Pro Lys Ser Pro Gly Glu Lys Thr
                115                 120                 125
Arg Tyr Asp Thr Ser Leu Gly Leu Leu Thr Lys Lys Phe Ile Tyr Leu
130                 135                 140
Leu Ser Glu Ser Glu Asp Gly Val Leu Asp Leu Asn Trp Ala Ala Glu
145                 150                 155                 160
Val Leu Asp Val Gln Lys Arg Ile Tyr Asp Ile Thr Asn Val Leu
                165                 170                 175
Glu Gly Ile Gln Leu Ile Arg Lys Lys Ala Lys Asn Asn Ile Gln Trp
                180                 185                 190
Val Gly Arg Gly Met Phe Glu Asp Pro Thr Arg Pro Gly Lys Gln Gln
            195                 200                 205
Gln Leu Gly Gln Glu Leu Lys Glu Leu Met Asn Thr Glu Gln Ala Leu
210                 215                 220
Asp Gln Leu Ile Gln Ser Cys Ser Leu Ser Phe Lys His Leu Thr Glu
225                 230                 235                 240
Asp Lys Ala Asn Lys Arg Leu Ala Tyr Val Thr Tyr Gln Asp Ile Arg
                245                 250                 255
Ala Val Gly Asn Phe Lys Glu Gln Thr Val Ile Ala Val Lys Ala Pro
            260                 265                 270
Pro Gln Thr Arg Leu Glu Val Pro Asp Arg Thr Glu Asp Asn Leu Gln
            275                 280                 285
Ile Tyr Leu Lys Ser Thr Gln Gly Pro Ile Glu Val Tyr Leu Cys Pro
290                 295                 300
Glu Glu Val Gln Glu Pro Asp Ser Pro Ser Glu Glu Pro Leu Pro Ser
305                 310                 315                 320
Thr Ser Thr Leu Cys Pro Ser Pro Asp Ser Ala Gln Pro Ser Ser Ser
                325                 330                 335
Thr Asp Pro Ser Ile Met Glu Pro Thr Ala Ser Ser Val Pro Ala Pro
            340                 345                 350
Ala Pro Thr Pro Gln Gln Ala Pro Pro Pro Ser Leu Val Pro Leu
            355                 360                 365
Glu Ala Thr Asp Ser Leu Leu Glu Leu Pro His Pro Leu Leu Gln Gln
370                 375                 380
Thr Glu Asp Gln Phe Leu Ser Pro Thr Leu Ala Cys Ser Ser Pro Leu
385                 390                 395                 400
Ile Ser Phe Ser Pro Ser Leu Asp Gln Asp Tyr Leu Trp Gly Leu
                405                 410                 415
Glu Ala Gly Glu Gly Ile Ser Asp Leu Phe Asp Ser Tyr Asp Leu Gly
            420                 425                 430
Asp Leu Leu Ile Asn
            435

<210> SEQ ID NO 2
<211> LENGTH: 11
<212> TYPE: PRT
```

```
<213> ORGANISM: Human immunodeficiency virus

<400> SEQUENCE: 2

Tyr Gly Arg Lys Lys Arg Arg Gln Arg Arg Arg
1               5                   10
```

METHODS OF USING E2F2 FOR THE TREATMENT OF HYPERTENSION

CROSS-REFERENCE TO RELATED APPLICATION

This application is the U.S. National Phase application, pursuant to 35 U.S.C. §371, of PCT International Application Ser. No. PCT/US2007/022804, filed Oct. 29, 2007, and published in English as WO 2008/057313, which claims the benefit of U.S. Provisional Application Nos.: 60/855,005, filed Oct. 27, 2006, and 60/855,986, filed Oct. 31, 2006, the entire contents of each of which are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 17, 2012, is named 66860714.txt and is 4,493 bytes in size.

BACKGROUND OF THE INVENTION

Hypertension contributes to progressive cardiac dysfunction and ultimately heart failure. Heart failure affects over 5 million Americans, with more than 500,000 new diagnoses annually in the United States alone, and remains the leading cause of death. Nearly half of these patients have hypertension and cardiac hypertrophy with apparent preservation of contraction of the heart, a syndrome for which there are currently no specifically tested and approved treatments. Improved therapeutic compositions and methods for the treatment of cardiac conditions, such as cardiac hypertrophy, are urgently required.

SUMMARY OF THE INVENTION

As described below, the present invention generally features compositions that feature an E2F family member, such as an E2F2 polypeptide or nucleic acid molecule, and related methods of treating or preventing hypertension, pulmonary hypertension, and cardiac failure.

In one aspect, the invention provides a fusion polypeptide containing a polypeptide having at least 85%, 90%, or 95% amino acid identity to an E2F polypeptide and a protein transduction domain, analog, or fragment thereof.

In another aspect, the invention provides a fusion polypeptide containing at least a fragment of an E2F2 polypeptide (SEQ ID NO: 1) operably linked to a protein transduction domain, analog, or fragment thereof. In a particular embodiment, the fusion polypeptide according to the aspects of the invention further contains a detectable domain.

In another aspect, the invention provides an expression vector that contains a nucleic acid sequence encoding the polypeptide according to any one of the aspects of the invention. In one embodiment, the expression vector further contains a promoter operably linked to the nucleic acid sequence. In a related embodiment, the promoter is positioned for expression in a bacterial or mammalian cell.

In another aspect, the invention provides a host cell that contains the fusion protein of any one of the aspects of the invention. In particular embodiments, the host cell contains the expression vector encoding the polypeptide of any one of the aspects of the invention. In certain embodiments, the host cell is a prokaryotic cell or a eukaryotic cell. In other embodiments, the host cell is any one or more of a bacterial cell, a mammalian cell, an insect cell, and a yeast cell. In particular embodiments, the cell is a human cell. In other particular embodiments, the cell is a cardiac cell or an endothelial cell.

In other aspects, the invention teaches a method for producing an E2F2 fusion polypeptide, the method involving providing a cell transformed with the isolated nucleic acid molecule comprising a nucleic acid sequence encoding the polypeptide of any one of the aspects of the invention described herein, positioned for expression in the cell, and culturing the cell under conditions for expressing the nucleic acid molecule, and then isolating the polypeptide.

In another aspect, the invention teaches methods of reducing hypertension in a subject in need thereof, the method involving administering an effective amount of an E2F2 polypeptide or an agent that increases E2F2 expression or biological activity to the subject.

In still another aspect, the invention teaches a method of treating or preventing a cardiac condition in a subject in need thereof, the method involving administering an effective amount of an E2F2 polypeptide or an agent that increases E2F2 expression or biological activity to the subject. In one embodiment, the E2F2 polypeptide comprises or consists essentially of at least a fragment of an E2F2 polypeptide that activates an ECE-1b promoter. In another particular embodiment of the aspect, the E2F2 fusion polypeptide comprises or consists essentially of at least a fragment of an E2F2 that activates an ECE-1b promoter and a protein transduction domain.

In another aspect, the invention features a method of treating hypertension or a cardiac condition in a subject, the method involving identifying a subject that is in need of treatment for hypertension or a cardiac condition, selecting the identified subject for treatment of hypertension or a cardiac condition, and then administering an agent that increases E2F2 expression or activity to the subject, thereby treating hypertension or a cardiac condition in the subject.

In still another aspect, the invention teaches a method of preventing hypertension or a cardiac condition in a subject having a propensity to develop hypertension, the method involving administering to the subject an effective amount of an E2F2 polypeptide, E2F2 fusion polypeptide, or agent that increases E2F2 expression or biological activity thereby preventing hypertension or a cardiac condition.

A further aspect of the invention features a method of reducing hypertension or ameliorating a cardiac condition in a subject having hypertension, the method involving administering to the subject an effective amount of an E2F2 polypeptide, E2F2 fusion polypeptide, or agent that increases E2F2 expression or biological activity thereby preventing hypertension or ameliorating a cardiac condition.

Another particular aspect of the invention features a method of increasing cardiac function in a subject in need thereof, the method involving administering an effective amount of E2F2 or an agent that increases E2F2 expression or activity to the subject. In one embodiment of the method, a further step is involved that includes measuring one or more of the following: relaxation rate, cardiac contractility, cardiac ejection volume, or end-systolic volume, where a change in relaxation rate, cardiac contractility, cardiac ejection volume, or end-systolic volume is indicative of treatment. In a related embodiment, the method reduces pulmonary hypertension. In a further embodiment, the E2F2 activator is administered systemically.

In another aspect, the invention teaches a method for increasing endothelin converting enzyme-1 expression or activity in a cell, the method involving contacting the cell with a polypeptide containing at least a fragment of an E2F2 polypeptide that binds to the endothelin converting enzyme-1b (ECE-1b) promoter, thereby increasing endothelin converting enzyme in a cell.

In another aspect, the invention features a method for increasing endothelin converting enzyme-1 expression or activity in a cell, the method involving contacting the cell with a nucleic acid molecule encoding at least a fragment of an E2F2 polypeptide that binds to the endothelin converting enzyme-1b (ECE-1b) promoter, thereby increasing endothelin converting enzyme in a cell. In one embodiment, the E2F2 polypeptide is linked to a protein transduction domain.

A further aspect of the invention teaches a method for ameliorating hypertension or a cardiac condition in a subject in need thereof, the method involving administering to a cell of the subject an expression vector comprising a nucleic acid molecule encoding an E2F2 polypeptide, and expressing the E2F2 polypeptide in the cell, thereby ameliorating the hypertension or cardiac condition.

In another aspect, the invention features a method for ameliorating hypertension or a cardiac condition in a subject in need thereof, the method involving administering to a cell of the subject an expression vector comprising a nucleic acid molecule encoding an E2F2 fusion polypeptide operably linked to a protein transduction domain, analog, or fragment thereof, and expressing the E2F2 fusion polypeptide in the cell, thereby ameliorating the hypertension or cardiac condition. In one embodiment, the cell is a human cell. In a related embodiment, the cell is a cardiac cell or an endothelial cell.

In a further aspect, the invention teaches a screening method for identifying agents that increase ECE-1B expression, the method involving contacting a cell expressing E2F2 and containing a reporter construct containing an ECE-1B promoter operably linked to a detectable reporter, and then detecting an increase in expression of the reporter, thereby identifying an agent that increases ECE-1B expression. In a particular embodiment, the method identifies an agent that prevents or ameliorates a cardiac condition, heart failure, hypertension, or pulmonary hypertension.

In another aspect, the invention features a pharmaceutical composition for the treatment of hypertension or a cardiac condition, the composition containing an effective amount of an E2F2 polypeptide or a nucleic acid molecule encoding an E2F2 polypeptide in a pharmaceutically acceptable excipient.

In a further aspect, the invention features a pharmaceutical composition for the treatment of hypertension or a cardiac condition containing an effective amount of at least a fragment of an E2F2 polypeptide fused to a protein transduction domain or a nucleic acid molecule encoding the E2F2 fusion polypeptide in a pharmaceutically acceptable excipient.

In another aspect, the invention features a kit for the treatment or prevention of hypertension or a cardiac condition containing an effective amount of an E2F2 polypeptide or a nucleic acid molecule encoding an E2F2.

In still a further aspect, the invention features a kit for the treatment of hypertension or a cardiac condition containing at least a fragment of an E2F2 polypeptide fused to a protein transduction domain or a nucleic acid molecule encoding the E2F2 fusion polypeptide.

In various embodiments of the above aspects, the hypertension is pulmonary hypertension. In a related embodiment, the hypertension is associated with a cardiovascular condition. In another related embodiment, the cardiovascular condition is cardiac failure.

In another aspect, the invention features a kit containing an E2F2 polypeptide or E2F2 fusion polypeptide in a pharmaceutically acceptable excipient, where the pharmaceutical system is labeled for use in the treatment or prevention of a cardiac condition. In one embodiment, the cardiac condition is cardiac failure.

In a further aspect, the invention features a kit containing an E2F2 polypeptide or E2F2 fusion polypeptide, where the pharmaceutical system is labeled for use in the enhancement of cardiac function.

In a particular embodiment, any of the above kits further contain written instructions for administering the composition to a subject for the treatment or prevention of hypertension or a cardiac condition.

In various embodiments of any of the previous aspects, an E2F polypeptide or fragment thereof is an E2F2 polypeptide that regulates hypertension or that binds to or otherwise regulates ECE-1b promoter activity. In other embodiments of the above aspects, the E2F2 polypeptide or E2F2 fusion polypeptide is a human or murine E2F2 polypeptide. In still other embodiments, the E2F2 polypeptide or E2F2 fusion polypeptide further comprises a sequence tag for purification. In further embodiments, the fusion protein comprises a protein transduction domain (e.g., a TAT domain).

In other embodiments of any previous aspect, the E2F2 transcription factor has at least 80%, 85%, 90%, 95% or even 100% sequence identity to an exemplary E2F2 polypeptide. In further embodiments, the E2F2 transcription factor comprises or consists essentially of at least a fragment of an E2F2 polypeptide and a protein transduction domain (e.g., a TAT domain). In certain various embodiments of any previous aspects, the detectable domain is selected from the group consisting of green fluorescent protein, red fluorescent protein, glucuronidase (GUS), luciferase, chloramphenicol transacetylase (CAT), and beta-galactosidase.

In other certain embodiments of any previous aspects, the polypeptide further comprises an amino acid sequence tag that facilitates purification of the polypeptide. In particular embodiments, the sequence tag is hexahistidine or glutathione S-transferase. In various embodiments of any previous aspects, the host cell is a cardiac cell or an endothelial cell. In other various embodiments of any previous aspects, the hypertension is pulmonary hypertension. In other embodiments of any previous aspects, the hypertension is pulmonary hypertension. In other embodiments of any previous aspects, the cardiac condition heart failure. In further various embodiments of any of the previous aspects, the method reduces blood pressure to 140/90, 130/80, 120/70 or to approximately normal levels.

In certain embodiments of any of these previous aspects, the method increases ECE-1b expression or activity by at least 10%, 20%, 30%, 50%, 75% or more relative to the expression or activity in an untreated control cell or reference condition. In other certain embodiments, the agent is an E2F2 fusion protein (e.g., E2F2 fused to a protein transduction domain). In other embodiments of any of these previous aspects, the E2F2 fusion protein comprises at least a fragment of an E2F2 polypeptide and a TAT protein transduction domain.

In other embodiments of any of the previous aspects, the hypertension is associated with a cardiovascular condition selected from any one or more of cardiac hypertrophy, reduced systolic function, reduced diastolic function, maladaptive hypertrophy, heart failure with preserved systolic function, diastolic heart failure, hypertensive heart disease, aortic and mitral valve disease, pulmonary valve disease, hypertrophic cardiomyopathy, hypertrophic cardiomyopathy, post ischemic and post-infarction cardiac remodeling and cardiac failure.

In other various embodiments of any of the previous aspects, the cardiac condition is selected from the group consisting of: cardiac failure, cardiac hypertrophy, reduced systolic function, reduced diastolic function, maladaptive hypertrophy, heart failure with preserved systolic function, diastolic heart failure, hypertensive heart disease, aortic stenosis, hypertrophic cardiomyopathy, and post ischemic cardiac remodeling.

Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "endothelin converting enzyme 1 (ECE1) protein" is meant an amino acid sequence having at least about 85% identity to GenBank Accession No. NP 001388 and having endothelin-1 activating activity.

By "endothelin converting enzyme 1 (ECE1) nucleic acid molecule" is meant a gene encoding an ECE1 protein. An exemplary human ECE1 gene is provided at GenBank Accession No. NM_001397. ECE1 nucleic acid molecules, promoters, and polypeptides are described, for example, in each of the following references, each of which is incorporated herein by reference in its entirety: Shimada et al., Cloning and functional expression of human endothelin-converting enzyme cDNA, *Biochem. Biophys. Res. Commun.* 207: 807-812, 1995; Valdenaire et al., A fourth isoform of endothelin-converting enzyme (ECE-1) is generated from an additional promoter: molecular cloning and characterization. *Europ. J. Biochem.* 264: 341-349, 1999; Valdenaire et al., Organization of the gene encoding the human endothelin-converting enzyme (ECE-1). *J. Biol. Chem.* 270: 29794-29798, 1995.

By "ECE-1b" promoter is meant at least a fragment upstream of a nucleic acid sequence encoding an ECE-1 polypeptide. In one embodiment, the "ECE-1b promoter" comprises at least 350, 400, 500, 750, 800, 822, 900, or 1000 base pairs upstream of a ECE-1b coding sequence.

By "E2F transcription factor" is meant any one of E2Fs 1-6 capable of binding an ECE-1b promoter and regulating expression of a downstream sequence.

By "E2F2 polypeptide" is meant an amino acid sequence having at least 85% amino acid sequence identity to GenBank Accession No. Q14209 that regulates expression of an ECE-1b promoter.

An exemplary sequence of an E2F2 polypeptide is provided below:

1 mlqgpralas aagqtpkvvp amsptelwps glsspqlcpa tatyytplyp qtappaaapg
61 tcldatphgp egqvvrclpa grlpakrkld legigrpvvp efptpkgkci rvdglpspkt
121 pkspgektry dtslglltkk fiyllsesed gvldlnwaae vldvqkrriy ditnvlegiq
181 lirkkaknni qwvgrgmfed ptrpgkqqql gqelkelmnt eqaldqliqs cslsfkhlte
241 dkankrlayv tyqdiravgn fkeqtviavk appqtrlevp drtednlqiy lkstqgpiev
301 ylcpeevqep dspseeplps tsticpspds aqpssstdps imeptassvp apaptpqqap
361 pppslvplea tdsllelphp llqqtedqfl sptlacsspl isfspsldqd dylwgleage
421 gisdlfdsyd lgdllin (SEQ ID NO:1)

Exemplary human E2F2 expression plasmids and methods for generating such plasmids are described, for example by, DeGregori et al., *Proc. Natl. Acad. Sci. USA*, 94: 7245-7250, 1997; by Johnson et al., *Nature* 365:349-352, 1993; and by Joyce et al., *Investigative Ophthalmology and Visual Science.* 2004; 45:1340-1348, each of which is incorporated herein by reference in its entirely. In one embodiment, the E2F2 polypeptide increases expression of the ECE-1b promoter by "activating" the promoter.

By "E2F2 nucleic acid molecule" is meant a polynucleotide that encodes at least a fragment of an E2F2 polypeptide.

By "E2F2 biological activity" is meant the regulation of vascular contractility, or ECE-1b promoter binding or regulation.

By "cardiac condition" is meant any cardiac disease or disorder.

By "disease" is meant any condition or disorder that damages or interferes with the normal function of a cell, tissue, or organ.

By "enhancing cardiac function" is meant producing a beneficial alteration in the pumping performance and capacity of the heart.

An "effective amount" is an amount sufficient to effect a beneficial or desired clinical result.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

The term "expression vector" is meant to include vectors which are capable of expressing DNA sequences contained therein, where such sequences are operably linked to other sequences capable of effecting their expression, i.e., promoter/operator sequences. In sum, "expression vector" is given a functional definition: any DNA sequence which is capable of effecting expression of a specified DNA code disposed therein. In general, expression vectors of utility in recombinant DNA techniques are often in the form of "plasmids" which refer to circular double stranded DNA loops which in their vector form are not bound to the chromosome. In the present specification, "plasmid" and "vector" are used interchangeably as the plasmid is the most commonly used form of vector. However, the invention is intended to include such other forms of expression vectors which function equivalently and which become known in the art subsequently.

The term "fragment" is meant to refer to a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The term "fusion protein" is meant to include a protein that combines at least two amino acid sequence that are not naturally contiguous.

The term "increases or decreases" is meant a positive or negative alteration. Such alterations are by 5%, 10%, 25%, 50%, 75%, 85%, 90% or even by 100% of a reference value.

The term "modulation" is meant to include any alteration (e.g., increase or decrease) in a biological function or activity.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

The term "positioned for expression" is meant that the polynucleotide of the invention (e.g., a DNA molecule) is positioned adjacent to a DNA sequence that directs transcription and translation of the sequence (i.e., facilitates the production of for example, a recombinant polypeptide of the invention, or an RNA molecule).

The term "promoter" is meant to refer to a polynucleotide sufficient to direct transcription. Exemplary promoters include nucleic acid sequences of lengths 100, 250, 300, 400, 500, 750, 900, 1000, 1250, and 1500 nucleotides that are upstream (e.g., immediately upstream) of the translation start site.

By "protein transduction domain" is meant an amino acid sequence that facilitates protein entry into a cell or cell organelle. Exemplary protein transduction domains include but are not limited to a minimal unidecapeptide protein transduction domain (corresponding to residues 47-57 of HIV-1 TAT comprising YGRKKRRQRRR(SEQ ID NO:2)), a polyarginine sequence comprising a number of arginines sufficient to direct entry into a cell (e.g., 3, 4, 5, 6, 7, 8 or 9 arginines), a VP22 domain (Zender et al., *Cancer Gene Ther*. 2002 June; 9(6):489-96), and an antennapedia protein transduction domain (Noguchi et al., Diabetes 2003; 52(7):1732-1737). See, also, *Nat Biotechnol*. 2001 December;19(12):1173-6.

The term "reduce" or "increase" is meant to alter negatively or positively, respectively, by at least 5%. An alteration may be by 5%, 10%, 25%, 30%, 50%, 75%, or even by 100%.

The term "subject" is meant to refer to a mammal, including, but not limited to, a human or non-human mammal, such as a bovine, equine, canine, ovine, or feline.

The term "treat" is meant decrease, suppress, attenuate, diminish, arrest, or stabilize the development or progression of a disease.

The term "polynucleotide" or "nucleic acid" as used herein refers to any nucleobase or nucleobase sequence, including mRNA, RNA, cRNA, cDNA or DNA. The term typically refers to oligonucleotides greater than 30 nucleotide residues in length.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

Bt the terms "polynucleotide variant" and "variant" are meant polynucleotides displaying substantial sequence identity with a reference polynucleotide sequence or polynucleotides that hybridize with a reference sequence under stringent conditions as known in the art (see for example Sambrook et al., Molecular Cloning. A Laboratory Manual", Cold Spring Harbor Press, 1989). These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally-occurring allelic variants.

By the terms "polypeptide", "peptide" and "protein" are meant to be used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally occurring amino acid polymers.

The term "polypeptide variant" is meant to refer to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

The term "recombinant polynucleotide" as used herein refers to a polynucleotide formed in vitro by the manipulation of a polynucleotide into a form not normally found in nature. For example, the recombinant polynucleotide can be in the form of an expression vector. Generally, such expression vectors include transcriptional and translational regulatory polynucleotide operably linked to the polynucleotide.

The term "recombinant polypeptide" is meant a polypeptide made using recombinant techniques, i.e., through the expression of a recombinant or synthetic polynucleotide.

The term "reporter molecule" as used in the present specification is meant a molecule that, by its chemical nature, provides an analytically identifiable signal that allows the detection of a complex comprising an antigen-binding molecule and its target antigen. The term "reporter molecule" also extends to use of cell agglutination or inhibition of agglutination such as red blood cells on latex beads, and the like.

The term "substantially identical" is meant to refer to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

In this disclosure, "comprises," "comprising," "containing" and "having" and the like can have the meaning ascribed to them in U.S. Patent law and can mean "includes," "including," and the like; "consisting essentially" of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

BRIEF DESCRIPTION OF THE DRAWINGS

FIG. 2A is a series of graphs showing the contractile response measured by the aortic ring assay in wild-type vs. mice lacking E2F2 ($E2F2^{-/-}$). FIG. 2B is a graph that shows the quantification of contraction expressed as percent against [30 mM] K+ treatment. Loss of E2F2 in the aortic artery leads to a hyper-contractility in response to ECE-1 substrate, big Endothelin-1 (ET-1). This novel function is specific to E2F2, independent of its cell cycle regulation, and appears to be dependent on Endothelin Converting Enzyme-1 (ECE-1) activity. Aortic ring assay was performed using endothelial-intact aortas isolated from E2F2-null mice and WT littermates to assess the ECE-1 bioactivity. KCL (30 mM)- or Phenylephrine ($10^{-9}$-$3\times10^{-6}$M)-induced contraction and acetylcholine ($10^{-9}$-$10^{-6}$M)-induced relaxation were similar between the two groups, the E2F2-null aortas demonstrated a significantly increased contractile response to Big ET ($2.7\times10^{-7}$ M to $2.1\times10^{-6}$ M). At maximum, E2F2-null aorta contracted to 80.0+18.81 vs. 26.5+6.77 by WT aorta (% Contraction/KCl, n=4, P<0.05), indicating a specific increase in ECE-1 activity due to the loss of E2F2.

FIG. 3A is a schematic diagram of the human ECE-1b promoter plasmid (pECE1b/C [or A]-alkaline phosphatase (AP)). FIG. 3B is a graph showing the results of alkaline phosphatase reporter assay with the human E2F2 plasmid (pE2F2) and human ECE-1b promoter plasmids. FIG. 3C is a graph showing alkaline phosphatase activity after siRNA-mediated endogenous E2F2 gene knockdown. The activity of the (C-338A) polymorphic form of ECE-1b promoter was significantly attenuated while the native form promoter activity was reduced to lesser extent (FIG. 3C). FIG. 3D shows the results of chromatin immunoprecipitation, which demonstrated that endogenous E2F2 occupies ECE-1b promoter region in vivo. These results suggest a direct regulation of ECE-1b transcription by endogenous E2F2 (FIG. 3D).

DETAILED DESCRIPTION OF THE INVENTION

Figure 1:
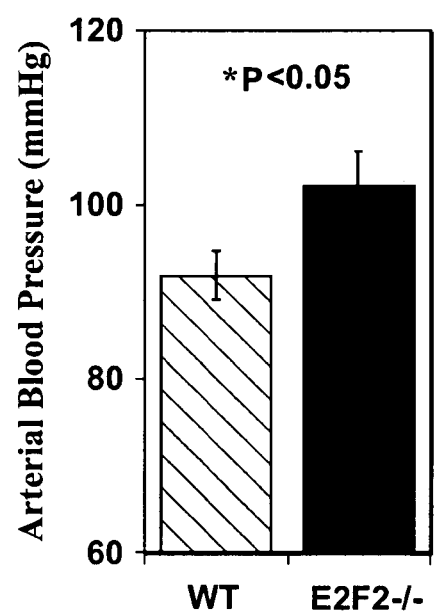
FIG. 1 is a graph showing that mice deficient in E2F2 are hypertensive. The arterial blood pressure (mmHg) of E2F2-null mice at 6 months old of age was measured by the tail cuff method. Blood pressure was significantly higher in E2F2-null mice (102.2+4.02 mmHg) compared to that of WT littermates (91.8+2.81 mmHg) (n=16, P<0.05).

The invention features compositions and methods that are useful for treating hypertension, including pulmonary hypertension, or a cardiac condition. The invention is based, at least in part, on the discovery that mice lacking E2F2 are hypertensive, and that in E2F2-null aortas show increased contractile response to full length endothelin-1. Endothelin converting enzyme 1 (ECE-1) is a metalloprotease responsible for the biogenesis of the potent vasoconstricting peptide endothelin-1 (ET-1). The ECE-1 promoter includes an E2F consensus site. As reported in more detail below, E2F2 induces expression of a reporter construct driven by the ECE-1 promoter, and a polymorphism present in the E2F consensus site disrupts the regulation of ECE-1 expression by E2F2. These studies indicate that E2F2 regulates blood pressure; and that deregulated E2F2 activity contributes to the pathogenesis of hypertension. Accordingly, treatment with agent that increase E2F2 expression or biological activity may lower blood pressure.

E2F Family of Transcription Factors

The transcription factor E2F was first identified as a nuclear factor capable of binding to the adenovirus E2 promoter. The E2F family of transcription factors plays a key role in regulating the mammalian cell cycle. They activate genes required for S-phase and in doing so can ultimately promote cell proliferation. E2F family members have been shown to be oncogenic, and E2F1 has been demonstrated to be a potent inducer of S-phase (Lam, E. W-F. et al. Current Opinion in Cell Biology 1994, 6: 859-866).

Six members of the E2F transcription factor family have been cloned, E2Fs 1-6. Representative E2F members include, but are not limited to, E2F1, E2F2, E2F3, E2F4, E2F5, E2F6 and E2F7 and their variants, including splice variants. E2F protein domains include the cyclin-binding domain, the DNA-binding domain, the transcription factor E2F/dimerisation partner (TDP) domain, the leucine zipper domain, the heterodimerisation domain, the trans-activation domain and the pocket protein binding domain). E2F exists as a heterodimeric complex in association with a dimeric partner protein, DP1 or DP2. This "free" E2F complex acts as a potent trans-activator of E2F-responsive genes. However, the activity of E2F is subject to regulation through inhibitory interactions with hypophosphorylated forms of the pocket proteins, pRb, p107 and p130, and controlled by complex transcriptional means.

E2F family of transcription factors play a pivotal role in cell cycle regulation; however the cardiovascular specific role is not well defined. ECE-1 is the main enzyme responsible for the biogenesis of the potent vasoconstricting peptide endothelin-1 (ET-1). Recent studies have revealed that a polymorphism in Endothelin Converting Enzyme-1b (ECE-1b) promoter (C-338A), which is strongly associated with blood pressure (BP) values in hypertensive women, is located at an E2F consensus site, and increases the promoter affinity specifically for E2F2. However, it is unknown if E2F2 regulates blood pressure. ECE-1b has been shown to negatively regulate other active ECE-1 isoforms, therefore, it is of interest what the consequences of E2F2 deficiency on vascular response to ET precursor and BP in E2F2-null mice would be. As reported herein, disruptions in E2F2 activity are associated with hypertension. Accordingly, the invention provides methods for treating hypertension. E2F2 regulates ECE-1b expression and ECE-1-dependent vessel contractility. Further, modulation of the specific expression of ECE-1b may also provide an alternative therapy for human hypertension.

Hypertension

High blood pressure affects 1 in 4 American adults. Blood pressure is the force of blood pushing against blood vessel walls. The heart pumps blood into the arteries (blood vessels), which carry the blood throughout the body. High blood pressure, also termed hypertension, is dangerous because it makes the heart work harder to pump blood to the body and it contributes to hardening of the arteries or atherosclerosis. There are several categories of blood pressure, including: Normal (Less than 120/80), Prehypertension (120-139/80-89), Stage 1 hypertension (140-159/90-99), and Stage 2 hypertension (160 and above/100 and above). The exact causes of hypertension are not known. Several factors and conditions may play a role in its development, including smoking, obesity, lack of physical activity, too much dietary salt, older age, and genetics. There are usually no symptoms or signs of hypertension, and nearly one-third of those who have hypertension do not know that they have it. If a subject's blood pressure is extremely high, certain symptoms may be present, including, severe headache, fatigue or confusion, vision problems, chest pain, difficulty breathing, irregular heartbeat, and blood in the urine. Hypertension is a serious condition that can damage the blood vessels, and can eventually lead to several other conditions, including stroke, heart failure, heart attack, kidney failure, and vision problems.

Pulmonary arterial hypertension (PAH) is continuous high blood pressure in the pulmonary artery. The average blood pressure in a normal pulmonary artery is about 14 mmHg when the person is resting. In PAH, the average is usually greater than 25 mmHg.

PAH is a serious condition for which there are treatments but no cure. Treatment benefits many patients.

The pulmonary arteries are the blood vessels that carry oxygen-poor blood from the right ventricle in the heart to the small arteries in the lungs. In PAH, three types of changes may occur in the pulmonary arteries: (1) the muscles within the walls of the arteries may tighten up. This makes the inside of the arteries narrower. (2) The walls of the pulmonary arteries may thicken as the amount of muscle increases in some arteries. Scar tissue may form in the walls of arteries. As the walls thicken and scar, the arteries become increasingly narrow. (3) Tiny blood clots may form within the smaller arteries, causing blockages. There is less room for the blood to flow through these narrower arteries. The arteries may also stiffen. Over time, some of the arteries may become completely blocked.

The narrowing of the pulmonary arteries causes the right side of heart to work harder to pump blood through the lungs. Over time, the heart muscle weakens and loses its ability to pump enough blood for the body's needs. This is called right heart failure. Heart failure is the most common cause of death in people with PAH.

Primary pulmonary arterial hypertension (PPAH) is inherited or occurs for no known reason. Secondary pulmonary arterial hypertension (SPAH) either is caused by or occurs because of another condition. Such conditions include chronic heart or lung disease, blood clots in the lungs, or a disease like scleroderma. About 300 new cases of PPAH are diagnosed in the United States each year. SPAH is much more common.

Methods of Treatment

Provided by the present invention are methods of treating or preventing hypertension, including pulmonary hypertension, or a cardiac condition in a subject in need thereof comprising administering an effective amount of E2F2, an E2F2 fusion polypeptide, or an agent that increases E2F2 expression or biological activity in a subject. In certain embodiments, the methods of treating hypertension (e.g., pulmonary hypertension) or a cardiac condition in a subject comprise identifying a subject that is in need of treatment the condition, selecting the identified subject for treatment of hypertension or a cardiac condition, and then administering an agent that increases E2F2 expression or activity to the subject, thereby treating hypertension or a cardiac condition in the subject.

Also provided in the invention are methods of preventing hypertension or a cardiac condition in a subject having a propensity to develop hypertension or a cardiac condition. The methods can comprise administering to the subject an effective amount of an E2F2 activator, wherein the administration of the activator prevents hypertension or a cardiac condition. The methods of the invention also include methods of reducing hypertension or ameliorating a cardiac condition in a subject in need thereof, the method comprising administering to the subject an effective amount of an E2F2 polypeptide, E2F2 fusion polypeptide, or agent that increases E2F2 expression or activity, wherein the administration of the activator reduces or ameliorates hypertension or the cardiac condition.

Hypertension as treated by the methods of the invention can be pulmonary hypertension. Arterial hypertension is another type of hypertension. The cardiac condition as treated by the methods of the invention can be, but is not limited to, heart failure. Hypertension can by associated with a cardiovascular condition. For example, hypertension can be associated with a cardiovascular condition selected from the group consisting of cardiac hypertrophy, reduced systolic function, reduced diastolic function, maladaptive hypertrophy, heart failure with preserved systolic function, diastolic heart failure, hypertensive heart disease, aortic and mitral valve disease, pulmonary valve disease, hypertrophic cardiomyopathy, hypertrophic cardiomyopathy, post ischemic and post-infarction cardiac remodeling and cardiac failure.

The invention also encompasses methods of enhancing cardiac function in a subject in need thereof, the method comprising administering an effective amount of E2F2 or an agent that increases E2F2 expression or activity to the subject.

In certain specific embodiments, the E2F2 activator is an E2F2 fusion protein. The fusion protein can comprise at least a fragment of an E2F2 polypeptide and a protein.

It may be desirable to measure output or readout of the invention. For example, it may be desirable to measure the effect of an agent, for example an E2F2 activator, on hypertension or cardiac function. Therefore, the methods of the invention may include further steps of measuring blood pressure, relaxation rate, cardiac contractility, cardiac ejection volume, or end-systolic volume, wherein a change in relaxation rate, cardiac contractility, cardiac ejection volume, or end-systolic volume is indicative of treatment. Methods of measuring cardiovascular function are known in the art and described herein.

Cardiovascular Function

Cardiac conditions, such as cardiac hypertrophy, reduced systolic function, reduced diastolic function, maladaptive hypertrophy, heart failure with preserved systolic function, diastolic heart failure, hypertensive heart disease, aortic and mitral valve disease, pulmonary valve disease, hypertrophic cardiomyopathy (e.g., hypertrophic cardiomyopathy originating from a genetic or a secondary cause), post ischemic and post-infarction cardiac remodeling and cardiac failure, are associated with maladaptive cardiac alterations, cardiac chamber, cellular, and molecular remodeling. Compositions of the invention may be used to enhance cardiac function in a subject having reduced cardiac function. Desirably, cardiac function is increased by at least 5%, 10% or 20%, or even by as much as 25%, 50% or 75%. Most advantageously, cardiac function is enhanced or damage is reversed, such that the function is substantially normal (e.g., 85%, 90%, 95%, or 100% of the cardiac function of a healthy control subject). Alternatively, such assays are used to monitor the condition of a subject prior to, during, or following treatment with an E2F2 polypeptide including a fusion polypeptide or an agent that increases E2F2 expression or activity. Treatments that increase cardiac function are useful in the methods of the invention.

Any number of standard methods are available for assaying cardiovascular function. Preferably, cardiovascular function in a subject (e.g., a human) is assessed using non-invasive means, such as measuring net cardiac ejection (ejection fraction, fractional shortening, and ventricular end-systolic volume) by an imaging method such echocardiography, nuclear or radiocontrast ventriculography, or magnetic resonance imaging, and systolic tissue velocity as measured by tissue Doppler imaging. Systolic contractility can also be measured non-invasively using blood pressure measurements combined with assessment of heart outflow (to assess power), or with volumes (to assess peak muscle stiffening). Measures of cardiovascular diastolic function include ventricular compliance, which is typically measured by the simultaneous measurement of pressure and volume, early diastolic left ventricular filling rate and relaxation rate (can be assessed from echoDoppler measurements). Other measures of cardiac function include myocardial contractility, resting stroke volume, resting heart rate, resting cardiac index (cardiac output per unit of time [L/minute], measured while seated and divided by body surface area [$m^2$])) total aerobic capacity, cardiovascular performance during exercise, peak exercise capacity, peak oxygen ($O_2$) consumption, or by any other method known in the art or described herein. Measures of vascular function include determination of total ventricular afterload, which depends on a number of factors, including peripheral vascular resistance, aortic impedance, arterial compliance, wave reflections, and aortic pulse wave velocity, Methods for assaying cardiovascular function include any one or more of the following: Doppler echocardiography, 2-dimensional echo-Doppler imaging, pulse-wave Doppler, continuous wave Doppler, oscillometric arm cuff, tissue Doppler imaging, cardiac catheterization, magnetic resonance imaging, positron emission tomography, chest X-ray, X-ray contrast ventriculography, nuclear imaging ventriculography, computed tomography imaging, rapid spiral computerized tomographic imaging, 3-D echocardiography, invasive cardiac pressures, invasive cardiac flows, invasive cardiac cardiac pressure-volume loops (conductance catheter), non-invasive cardiac pressure-volume loops.

E2F2 Polypeptides and Polynucleotides

As described herein, the present invention features methods of treating or preventing hypertension, pulmonary hypertension, and a cardiac condition, such as cardiac failure featuring E2F2 or an agent that increases the expression or activity of an E2F2 polypeptide. One method for increasing E2F2 activity is by administering an E2F2 polypeptide directly to a subject or administering a nucleic acid molecule encoding E2F2 polypeptide to a subject. Accordingly, the invention provides therapies including polynucleotide and protein-based therapeutics useful for preventing hypertension, pulmonary hypertension, and cardiac failure in a subject.

In one embodiment, a recombinant polypeptide of the invention comprises a polypeptide having at least 85% amino acid identity to an E2F polypeptide, analog, or fragment thereof. In another working embodiment, an E2F2 polypeptide of the invention comprises a polypeptide having at least 50%, 55%, 60%, 65%, 70%, 75%, 80%, 85%, 90%, 95%, 96%, 97%, 98%, 99% amino acid identity to a reference E2F2 polypeptide. In other embodiments, the fusion polypeptide of the invention is a human or murine E2F2. The E2F2 polypeptide of the invention acts as an ECE-1b activator, thus, when the E2F2 fusion polypeptide contacts a cell, ECE-1b expression or activity is increased relative to ECE-1b expression or activity in an untreated control cell or other reference.

Protein-Based Therapeutics

In one approach, the invention provides a protein-based therapeutic of the invention that features an E2F2 polypeptide fused to a protein transduction domain, where the protein transduction domain is capable of acting as a "molecular passport" to permit entry into cells of a biologically active E2F2 transcription factor. In one embodiment, the fusion protein comprises a full-length E2F2 polypeptide fused to a protein transduction domain. In other embodiments, the E2F2 fusion polypeptide comprises at least a fragment of an E2f2 polypeptide (e.g., at least about Protein transduction domains are short peptide sequences that enable proteins to translocate across the cell and nuclear membranes, leading to entry into the cytosol by means of atypical secretory and internalization pathways (Joliot et al., Nat Cell Biol 2004; 6(3):189-196). In 1988 Green and Loewenstein discovered that the human immunodeficiency virus type 1 (HIV-1) TAT-protein, an 86-amino acid protein, could rapidly enter cells and was even capable of entering the cell nucleus (Green and Loewenstein P M. Cell 1988; 55(6): 1179-1188). Building on this observation, a minimal unidecapeptide protein transduction domain (corresponding to residues 47-57 of HIV-1 TAT) was developed by Dowdy and co-workers (Schwarze et al., Science 1999; 285(5433):1569-1572). This unidecapeptide sequence was used successfully to deliver an NH2-terminal TAT-β-galactosidase fusion protein (120 kDa) to mouse tissues via intraperitoneal injections into mice (Schwarze et al., Science 1999; 285(5433):1569-1572). The TAT-β-galactosidase fusion protein retained biological activity. This general method has now been successfully used for the transduction of a variety of proteins. PTD-containing peptides or proteins are taken up by cells within 5 minutes at concentrations as low as 100 nM as assessed by direct labeling with fluorescein or by indirect immunofluorescence using antibodies. This uptake is independent of endocytotic mechanisms, transmembrane protein channels, and protein receptor binding. In addition, in vitro studies have demonstrated that protein transduction domain-mediated translocation occurs at low temperatures and exhibits no strong cellular specificity.

As described in more detail below, virtually any E2F2 polypeptide can be fused to a protein transduction domain and used for protein therapy. Advantageously, such fusion proteins can be delivered to cells in vitro or in vivo. In one embodiment, a fusion protein of the invention is used to contact a cell in vitro, such that the cell takes up the fusion protein. The cell is subsequently delivered to a subject for a therapeutic purpose. Alternatively, an E2F2-PTD fusion protein of the invention is administered to a cell, tissue, or organ in situ, such that the cell; tissue, or organ takes up the fusion protein to achieve a therapeutic purpose.

E2F2 Polypeptides and Nucleic Acid Molecules

Recombinant E2F2 polypeptides and fusion polypeptides of the invention are produced using virtually any method known to the skilled artisan. Typically, recombinant polypeptides are produced by transformation of a suitable host cell with all or part of a polypeptide-encoding nucleic acid molecule or fragment thereof in a suitable expression vehicle. Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*). In general, prokaryotes are preferred for cloning of DNA sequences in constructing the vectors useful in the invention. For example, *E. coli* K12 strain 294 (ATCC No. 31446) is particularly useful. Other microbial strains which may be used include *E. coli* strains such as *E. coli* B, and *E. coli* X1776 (ATTC No. 31537). The aforementioned strains, as well as *E. coli* W3110 (ATTC No. 27325), bacilli such as *Bacillus subtilus*, and other enterobacteriaceae such as *Salmonella typhimurium* or *Serratia marcesans*, and various pseudomonas species may be used. These examples are intended to be illustrative rather than limiting. In general, plasmid vectors containing replicon and control sequences which are derived from species compatible with the host cell are used in connection with these hosts. The vector ordinarily carries a replication site, as well as marking sequences which are capable of providing phenotypic selection is transformed cells. For example, *E. coli* is typically transformed using pBR 322, a plasmid derived from an *E. coli* species (Bolivar, et al., Gene 2: 95 (1977)). pBR322 contains genes for ampicillin and tetracycline resistance and thus provides easy means for identifying transformed cells. The pBR322 plasmid, or other microbial plasmid must also contain, or be modified to contain, promoters which can be used by the microbial organism for expression of its own proteins. Those promoters most commonly used in recombinant DNA construction include the .beta.-lactamase (penicillinase) and lactose promoter systems (Chang et al, Nature, 275: 615(1978), Itakura, et al, Science, 198: 1056 (1977); (Goeddel, et al Nature 281: 544 (1979) and a tryptophan (trp) promoter system (Goeddel, et al, Nucleic Acids Res., 8: 4057 (1980); EPO Appl Publ No. 0036776). While these are the most commonly used, other microbial promoters have been discovered and utilized, and details concerning their nucleotide sequences have been published, enabling a skilled worker to ligate them functionally with plasmid vectors (Siebenlist, et al, Cell 20: 269 (1980)).

Alternatively, the invention employs a eukaryotic host cell (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

One particular bacterial expression system for polypeptide production is the *E. coli* pET expression system (e.g., pET- 28) (Novagen, Inc., Madison, Wis). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Alternatively, recombinant polypeptides of the invention are expressed in *Pichia pastoris*, a methylotrophic yeast. *Pichia* is capable of metabolizing methanol as the sole carbon source. The first step in the metabolism of methanol is the oxidation of methanol to formaldehyde by the enzyme, alcohol oxidase. Expression of this enzyme, which is coded for by the AOX1 gene is induced by methanol. The AOX1 promoter can be used for inducible polypeptide expression or the GAP promoter for constitutive expression of a gene of interest.

In general, plasmid vectors containing replicon and control sequences which are derived from species compatible with the host cell are used in connection with these hosts. The vector ordinarily carries a replication site, as well as marking sequences which are capable of providing phenotypic selection is transformed cells. For example, *E. coli* is typically transformed using pBR322, a plasmid derived from an *E. coli* species (Bolivar, et al., Gene 2: 95 (1977)). pBR322 contains genes for ampicillin and tetracycline resistance and thus provides easy means for identifying transformed cells. The pBR322 plasmid, or other microbial plasmid must also contain, or be modified to contain, promoters which can be used by the microbial organism for expression of its own proteins. Those promoters most commonly used in recombinant DNA construction include the .beta.-lactamase (penicillinase) and lactose promoter systems (Chang et al, Nature, 275: 615 (1978), Itakura, et al, Science, 198: 1056 (1977); (Goeddel, et al Nature 281: 544 (1979) and a tryptophan (trp) promoter system (Goeddel, et al, Nucleic Acids Res., 8: 4057 (1980); EPO Appl Publ No. 0036776). While these are the most commonly used, other microbial promoters have been discovered and utilized, and details concerning their nucleotide sequences have been published, enabling a skilled worker to ligate them functionally with plasmid vectors (Siebenlist, et al, Cell 20: 269 (1980)).

In addition to prokaryotes, eukaryotic microbes, such as yeast cultures, may also be used. *Saccharomyces cerevisiae*, or common baker's yeast is the most commonly used among eukaryotic microorganisms, although a number of other strains are commonly available. For expression in *Saccharomyces*, the plasmid YRp7, for example, (Stinchcomb, et al, Nature, 282: 39 (1979); Kingsman et al, Gene 7: 141 (1979); Tschemper, et al, Gene 10: 157(1980)) is commonly used. This plasmid already contains the trp1 gene which provides a selection marker for a mutant strain of yeast lacking the ability to grow in tryptophan, for example ATCC No. 44076 or PEP4-1 (Jones, Genetics, 85: 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., J. Biol. Chem., 255 2073 (1980)) or other glycolytic enzymes (Hess, et al., J. Adv. Enzyme Reg., 7: 149 (1968); Hotland, et al, Biochemistry, 17: 4900 (1978)), such as enolase, glyceraldehyde-3-phosphatic dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters which have the additional advantage of transcription controlled by growth conditions are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid). Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [Tissue Culture, Academic Press, Kruse and Patterson, editors (1973)]. Examples of such useful host cell lines are VERO and HeLa cells, Chinese hamster ovary (CHO) cell lines, and W138, BHK, COS-7 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma. Adenovirus 2, and most frequently Simian Virus 40 (SV40). The early and late promoters of SV40 virus are particularly useful because both are obtained easily from the virus as a fragment which also contains the SV40 viral origin of replication (Fiers, et al, Nature, 273: 113 (1978) incorporated herein by reference. Smaller or larger SV40 fragments may also be used, provided there is included the approximately 250 by sequence extending from the Hind III site toward the BglI site located in the viral origin of replication. Further, it is also possible, and often desirable, to utilize promoter or control sequences normally associated with the desired gene sequence, provide such control sequences are compatible with the host cell systems.

An origin of replication may be provided either by construction of the vector to include an exogenous origin, such as may be derived from SV40 or other viral (e.g. Polyoma, Adeno, VSV, BPV, etc.) source, or may be provided by the host cell chromosomal replication mechanism. If the vector is integrated into the host cell chromosome, the latter is often sufficient.

The constructs of the instant invention can be introduced into suitable host cells for expression using any of a number of non-viral or viral gene delivery vectors. For example, retroviruses (in particular, lentiviral vectors) provide a convenient platform for gene delivery systems. A coding sequence of interest (for example, a sequence useful for gene therapy applications) can be inserted into a gene delivery vector and packaged in retroviral particles using techniques known in the art. Recombinant virus can then be isolated and delivered to cells of the subject either in vivo or ex vivo.

In one illustrative example, retroviruses provide a convenient and effective platform for gene delivery systems. A selected nucleotide sequence that encodes, for example, a polypeptide having at least 85% amino acid identity to E2F2; and a protein transduction domain, analog, or fragment thereof, can be inserted into a vector and packaged in retroviral particles using techniques known in the art. The recombinant virus can then be isolated and delivered to a subject. Several illustrative retroviral systems have been described examples of which include: U.S. Pat. No. 5,219,740; Miller and Rosman, 1989, Bio Techniques 7: 980-990; Miller, A. D., 1990, Human Gene Therapy 1: 5-14; Scarpa et al., 1991, Virology 180: 849-852; Burns et al., 1993, Proc. Natl. Acad. Sci. USA 90: 8033-8037; and Boris-Lawrie and Temin, 1993, Cur. Opin. Genet. Develop. 3: 102-109).

In addition, a number of adenovirus-based systems have been described. Unlike retroviruses which integrate into the host genome, adenoviruses persist extrachromosomally thus minimizing the risks associated with insertional mutagenesis (see, e.g., Haj-Ahmad and Graham, 1986, J. Virol. 57: 267-274; Bett et al., 1993, J. Virol. 67: 5911-5921; Mittereder et al., 1994, Human Gene Therapy 5: 717-729; Seth et al., 1994, J. Virol. 68: 933-940, Barr et al., 1994, Gene Therapy 1: 51-58; Berkner, K. L., 1988, Bio Techniques 6: 616-629; and Rich et al., 1993, Human Gene Therapy 4: 461-476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al., 1988, Molec. Cell. Biol. 8: 3988-3996; Vincent et al., 1990, Vaccines 90, Cold Spring Harbor Laboratory Press; Carter, B. J., 1992, Current Opinion in Biotechnology 3: 533-539; Muzyczka, N., 1992, Current Topics in Microbiol. and Immunol. 158: 97-129; Kotin, R. M., 1994, Human Gene Therapy 5: 793-801; Shelling and Smith, 1994, Gene Therapy 1: 165-169; and Zhou et al., 1994, J. Exp. Med. 179:1867-1875.

Additional viral vectors useful for delivering the polynucleotides encoding the E2F2 activator polypeptides of the present invention by gene transfer include those derived from the pox family of viruses, such as vaccinia virus and avian poxvirus. By way of example, vaccinia virus recombinants expressing an E2F2 activator polypeptide of the invention can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-BrdU and picking viral plaques resistant thereto.

Alternatively, avipoxviruses, such as the fowlpox and canarypox viruses, can also be used to deliver the coding sequences of interest. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al., J. Biol. Chem. 268:6866-69, 1993; and Wagner et al., Proc. Natl. Acad. Sci. USA 89:6099-6103, 1992, can also be used for gene delivery under the invention.

In other illustrative embodiments, lentiviral vectors are to deliver the E2F2 activator polypeptide-encoding polynucleotides into selected cells or tissues. Typically, these vectors comprise a 5' lentiviral LTR, a tRNA binding site, a packaging signal, a promoter operably linked to one or more genes of interest, an origin of second strand DNA synthesis and a 3' lentiviral LTR, wherein the lentiviral vector contains a nuclear transport element. The nuclear transport element may be located either upstream (5') or downstream (3') of a coding sequence of interest (for example, a synthetic Gag or Env expression cassette of the present invention). A wide variety of lentiviruses may be utilized within the context of the present invention, including for example, lentiviruses selected from the group consisting of HIV, HIV-1, HIV-2, FIV, BIV, EIAV, MVV, CAEV, and SIV. Illustrative examples of lentiviral vectors are described in PCT Publication Nos. WO 00/66759, WO 00/00600, WO 99/24465, WO 98/51810, WO 99/51754, WO 99/31251, WO 99/30742, and WO 99/15641. Desirably, a third generation SIN lentivirus is used. Commercial suppliers of third generation SIN (self-inactivating) lentiviruses include Invitrogen (ViraPower Lentiviral Expression System). Detailed methods for construction, transfection, harvesting, and use of lentiviral vectors are given, for example, in the Invitrogen technical manual "ViraPower Lentiviral Expression System version B 050102 25-0501", available on the world wide web at invitrogen.com/Content-/Tech-Online/molecular_biology/manuals_p-ps/virapower_lentiviral_system_ma-n.pdf. Lentiviral vectors have emerged as an efficient method for gene transfer. Improvements in biosafety characteristics have made these vectors suitable for use at biosafety level 2 (BL2). A number of safety features are incorporated into third generation SIN (self-inactivating) vectors. Deletion of the viral 3' LTR U3 region results in a provirus that is unable to transcribe a full length viral RNA. In addition, a number of essential genes are provided in trans, yielding a viral stock that is capable of but a single round of infection and integration. Lentiviral vectors have several advantages, including: 1) pseudotyping of the vector using amphotropic envelope proteins allows them to infect virtually any cell type; 2) gene delivery to quiescent, post mitotic, differentiated cells has been demonstrated; 3)

their low cellular toxicity is unique among transgene delivery systems; 4) viral integration into the genome permits long term transgene expression; 5) their packaging capacity (6-14 kb) is much larger than other retroviral, or adeno-associated viral vectors. In a recent demonstration of the capabilities of this system, lentiviral vectors expressing GFP were used to infect murine stem cells resulting in live progeny, germline transmission, and promoter-, and tissue-specific expression of the reporter (Ailles, L. E. and Naldini, L., HIV-i-Derived Lentiviral Vectors. In: Trono, D. (Ed.), Lentiviral Vectors, Springer-Verlag, Berlin, Heidelberg, N.Y., 2002, pp. 31-52). An example of the current generation vectors is outlined in FIG. 2 of a review by Lois et al. (Lois, C., Hong, E. J., Pease, S., Brown, E. J., and Baltimore, D., Germline transmission and tissue-specific expression of transgenes delivered by lentiviral vectors, Science, 295 (2002) 868-872).

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In other embodiments, a polynucleotide is administered/delivered as "naked" DNA, for example as described in Ulmer et al., Science 259:174549, 1993 and reviewed by Cohen, Science 259:1691-92, 1993. The uptake of naked DNA may be increased by coating the DNA onto biodegradable beads, which are efficiently transported into the cells.

A composition of the present invention may be delivered via a particle bombardment approach, many of which have been described. For example, gas-driven particle acceleration can be achieved with devices such as those manufactured by Powdeiject Pharmaceuticals PLC (Oxford, UK) and Powdeiject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest. Other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

If cells without formidable cell wall barriers are used as host cells, transfection is carried out by the calcium phosphate precipitation method as described by Graham and Van der Eb, Virology, 52: 546 (1978). However, other methods for introducing DNA into cells such as by nuclear injection or by protoplast may also be used.

If prokaryotic cells or cells which contain substantial cell wall constructions are used, the preferred method of transfection is calcium treatment using calcium chloride as described by Cohen, F. N. et al Proc. Natl. Acad. Sci. (USA), 69: 2110 (1972).

Construction of suitable vectors containing the desired coding and control sequences employ standard ligation techniques. Isolated plasmids or DNA fragments are cleaved, tailored, and relegated in the form desired to form the plasmids required.

Cleavage is performed by treating with restriction enzyme (or enzymes) in suitable buffer. In general, about 1 .mu.g plasmid or DNA fragments is used with about 1 unit of enzyme in about 20 .mu.l of buffer solution. (Appropriate buffers and substrate amounts for particular restrictions enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° C. with 10 units of Polymerase I (Klenow), phenol-chloroform extracted, and ethanol precipitated.

Size separation of the cleaved fragments is performed using 6 percent polyacrylamide gel described by Goeddel, D., et al, Nucleic Acids Res., 8: 4057 (1980) incorporated herein by reference.

For ligation approximately equimolar amounts of the desired components, suitably end tailored to provide correct matching are treated with about 10 units T4 DNA ligase per 0.5 .mu.g DNA. (When cleaved vectors are used as components, it may be useful to prevent religation of the cleaved vector by pretreatment with bacterial alkaline phosphatase.)

For analysis to confirm correct sequences in plasmids constructed, the ligation mixtures are used to transform *E. coli* K12 strain 294 (ATCC 31446), and successful transformants selected by ampicillin resistance where appropriate. Plasmids from the transformants are prepared, analyzed by restriction and/or sequenced by the method of Messing, et al, Nucleic Acids Res., 9:309 (1981) or by the method of Maxam, et al, Methods in Enzymology, 65:499 (1980).

Once the recombinant polypeptide of the invention is expressed, it is isolated, for example, using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra). Alternatively, the polypeptide is isolated using a sequence tag, such as a hexahistidine tag, that binds to nickel column.

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

E2F2 Analogs

Also included in the invention are modified E2F2 polypeptides and fusion polypeptides or fragments thereof. The modifications may enhance E2F2 activity (e.g., enhance ECE-1 expression), or increase protein solubility or yield. The invention provides methods for optimizing an E2F2 or protein transduction domain amino acid sequence or nucleic acid sequence by producing an alteration in the sequence. Such alterations may include certain mutations, deletions, insertions, or post-translational modifications. The invention further includes analogs of any naturally-occurring polypeptide of the invention. Analogs can, differ from a naturally-occurring polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino, acid sequence of the invention. The length of sequence comparison is at least 5, 10, 15 or 20 amino acid residues, preferably at least 25, 50, or 75 amino acid residues, and more preferably more than 100 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., beta. or .gamma. amino acids. Additionally, a detectable domain may be added to the fusion polypeptide. The detectable domain may be green fluorescent protein, red fluorescent protein, glucuronidase (GUS), luciferase, chloramphenicol transacetylase (CAT), or beta-galactosidase. The fusion polypeptide may further comprise an amino acid sequence tag that facilitates purification of the polypeptide. Examples include, but are not limited to, hexahistidine tags or glutathione S-transferase (GST).

In addition to full-length polypeptides, the invention also provides fragments of any one of the polypeptides or peptide domains of the invention. As used herein, the term "a fragment" means at least 5, 10, 13, or 15 amino acids. In other embodiments a fragment is at least 20 contiguous amino acids, at least 30 contiguous amino acids, or at least 50 contiguous amino acids, and in other embodiments at least 60 to 80, 100, 200, 300 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the E2F2 protein's functional activity. Such analogs are administered according to methods of the invention. E2F2 protein analogs may exceed the physiological activity of the original polypeptide. Methods of analog design are well known in the art, and synthesis of analogs can be carried out according to such methods by modifying the chemical structures such that the resultant analogs increase the reprogramming or regenerative activity of a reference transcription factor/protein transduction domain fusion polypeptide. These chemical modifications include, but are not limited to, substituting alternative R groups and varying the degree of saturation at specific carbon atoms of a reference fusion polypeptide. Preferably, the fusion protein analogs are relatively resistant to in vivo degradation, resulting in a more prolonged therapeutic effect upon administration.

Screening Methods

Included in the invention are methods of screening that can be used, for example, to identify agents useful for the treatment of a condition such as a cardiac condition, hypertension, or pulmonary hypertension. In preferred embodiments the invention encompasses screening methods for identifying agents that act as E2F2 activators.

In particular, the invention encompasses screening method for identifying agents that increase ECE-1B expression, the method comprising contacting a cell expressing E2F2 and comprising a reporter construct comprising an ECE-1B promoter operably linked to a detectable reporter, and then detecting an increase in expression of the reporter, thereby identifying an agent that increases ECE-1B expression. In certain embodiments, the method is used to identify agents that are useful for the treatment of a cardiac condition, hypertension, or pulmonary hypertension.

Methods of identifying agents that act as E2F2 activators are provided in which a purified preparation of an E2F2 protein is incubated in the presence and absence of a candidate agent under conditions in which the E2F2 is active, and the level of E2F2 activity is measured by a suitable assay. For example, an E2F2 activator can be identified by measuring the ability of a candidate agent to increase E2F2 activity in a cell. In one embodiment of this method, a cell that is capable of expressing an E2F2 gene is exposed to, or cultured in the presence and absence of, the candidate agent under conditions in which the E2F2 is active in the cells, and an activity relating to the cardiac condition or hypertension is detected. An agent tests positive if it inhibits this activity.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J.*

Med. Chem. 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

In still other embodiments, random peptide libraries consisting of all possible combinations of amino acids attached to a solid phase support may be used to identify peptides that are able to bind to a target molecule or to a functional domain thereof. Identification of molecules that are able to bind to a target molecule may be accomplished by screening a peptide library with a recombinant soluble target molecule. The target molecule may be purified, recombinantly expressed or synthesized by any suitable technique. Such molecules may be conveniently prepared by a person skilled in the art using standard protocols as for example described in Sambrook, et al., (1989, supra) in particular Sections 16 and 17; Ausubel et al., ("Current Protocols in Molecular Biology", John Wiley & Sons Inc, 1994-1998), in particular Chapters 10 and 16; and Coligan et al., ("Current Protocols in Immunology", (John Wiley & Sons, Inc, 1995-1997), in particular Chapters 1, 5 and 6. Alternatively, a target polypeptide according to the invention may be synthesized using solution synthesis or solid phase synthesis as described, for example, in Chapter 9 of Atherton and Shephard (supra) and in Roberge et al (1995, Science 269: 202).

In general, fusion polypeptides having E2F2 activating activity are identified from large libraries of natural product or synthetic (or semi-synthetic) extracts or chemical libraries or from polypeptide or nucleic acid libraries, according to methods known in the art. Such candidate polypeptides or the nucleic acid molecules encoding them may be modified to include a protein transduction domain. The modified polypeptides are then screened for the desired activity. Those skilled in the field of drug discovery and development will understand that the precise source of test extracts or compounds is not critical to the screening procedure(s) of the invention. Agents used in screens may include known compounds (for example, known polypeptide therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

To identify and isolate the peptide/solid phase support that interacts and forms a complex with a target molecule, suitably a target polypeptide, it may be necessary to label or "tag" the target polypeptide. The target polypeptide may be conjugated to any suitable reporter molecule, including enzymes such as alkaline phosphatase and horseradish peroxidase and fluorescent reporter molecules such as fluorescein isothyiocynate (FITC), phycoerythrin (PE) and rhodamine. Conjugation of any given reporter molecule, with target polypeptide, may be performed using techniques that are routine in the art. Alternatively, target polypeptide expression vectors may be engineered to express a chimeric target polypeptide containing an epitope for which a commercially available antigen-binding molecule exists. The epitope specific antigen-binding molecule may be tagged using methods well known in the art including labeling with enzymes, fluorescent dyes or colored or magnetic beads.

For example, the "tagged" target polypeptide conjugate is incubated with the random peptide library for 30 minutes to one hour at 22° C. to allow complex formation between target polypeptide and peptide species within the library. The library is then washed to remove any unbound target polypeptide. If the target polypeptide has been conjugated to alkaline phosphatase or horseradish peroxidase the whole library is poured into a petri dish containing a substrate for either alkaline phosphatase or peroxidase, for example, 5-bromo-4-chloro-3-indoyl phosphate (BCIP) or 3,3',4,4"-diamnobenzidine (DAB), respectively. After incubating for several minutes, the peptide/solid phase-target polypeptide complex changes color, and can be easily identified and isolated physically under a dissecting microscope with a micromanipulator. If a fluorescently tagged target polypeptide has been used, complexes may be isolated by fluorescent activated sorting. If a chimeric target polypeptide having a heterologous epitope has been used, detection of the peptide/target polypeptide complex may be accomplished by using a labeled epitope specific antigen-binding molecule. Once isolated, the identity of the peptide attached to the solid phase support may be determined by peptide sequencing.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have E2F2 activating activity, further fractionation of the positive lead extract is necessary to isolate molecular constituents responsible for the observed effect. Thus, the goal of the extraction, fractionation, and purification process is the careful characterization and identification of a chemical entity within the crude extract that has the E2F2 activating activity. Methods of fractionation and purification of such heterogeneous extracts are known in the art. If desired, compounds shown to be useful as therapeutics are chemically modified according to methods known in the art.

In another example, methods can be used to identify agents that increase ECE-1B expression, the method comprising contacting a cell expressing E2F2, and comprising a reporter construct comprising an ECE-1B promoter operably linked to a detectable reporter. Thus, detecting an increase in expression of the reporter would allow identification of an agent that increases ECE-1B expression. In preferred embodiments the method is used to identify agents that are useful for the treatment of a cardiac condition, hypertension, or pulmonary hypertension.

Promoter activity refers to the ability to initiate transcription. The level of promoter activity is quantifiable, for instance by assessment of the amount of mRNA produced by transcription from the promoter, or by assessment of the amount of protein product produced by translation of mRNA produced by transcription from the promoter. The amount of a specific mRNA present in an expression system may be determined for example using specific oligonucleotides which are able to hybridize with the mRNA and which are labeled or may be used in a specific amplification reaction such as the polymerase chain reaction. Use of a reporter gene facilitates determination of promoter activity by reference to protein production.

In such a construct, the promoter is operably linked to a gene, e.g. a coding sequence. Generally, the gene may be transcribed into mRNA which may be translated into a peptide or polypeptide product which may be detected and preferably quantitated following expression. A gene whose encoded product may be assayed following expression is termed a "reporter gene", i.e. a gene which "reports" on promoter activity.

The reporter gene preferably encodes an enzyme which catalyses a reaction which produces a detectable signal, preferably a visually detectable signal, such as a colored product. Many examples are known, including, but not limited to, alkaline phosphatase, beta-galactosidase and luciferase. The secreted alkaline phosphatase is widely used as reporter gene to analyze the activity of promoters and transcriptional factors and to tract gene expression in cell culture or animals. Alkaline phosphatase can be effectively secreted into culture medium and serum. This unique characteristic of alkaline phosphatase makes it convenient to kinetically analyze gene expression over a period of time using a single culture or animal. Beta-galactosidase activity may be assayed by production of blue color on substrate, the assay being by eye or by use of a spectrophotometer to measure absorbance. Fluorescence, for example that is produced as a result of luciferase activity, may be quantitated using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labeled directly or indirectly using any standard technique.

Those skilled in the art are well aware of a multitude of possible reporter genes and assay techniques which may be used to determine gene activity. Any suitable reporter/assay may be used and it should be appreciated that no particular choice is essential to, or a limitation of, the present invention.

Thus, nucleic acid constructs comprising a promoter and a reporter gene may be employed in screening for a substance able to act as an E2F2 activator, for example the nucleic acid constructs may be used in screening for a substance that can act modulate the transcriptional activator activity of E2F2 on the ECE-1b promoter. For therapeutic purposes, e.g. for treatment of hypertension or a cardiac condition, a substance able to inhibit expression of the promoter, i.e. antagonize the stimulator function of E2F, may be sought. A method of screening for ability of a substance to increase ECE-1b expression may comprise contacting an expression system, such as a host cell, containing a nucleic acid construct as discussed with a test or candidate substance and determining expression of the reporter gene. The level of expression in the presence of the test substance may be compared with the level of expression in the absence of the test substance. A difference in expression in the presence of the test substance may indicate ability of the substance to act as an E2F2 activator.

A promoter construct may be introduced into a cell line using any technique previously described to produce a stable cell line containing the reporter construct integrated into the genome. The cells may be grown and incubated with test compounds for varying times. The cells may be grown in 96 well plates to facilitate the analysis of large numbers of compounds. The cells may then be washed and the reporter gene expression analyzed. For some reporters, such as luciferase the cells will be lysed then analyzed. Preliminary assays in vitro may be followed by, or run in parallel with, in vivo assays.

The person skilled in the art will design any appropriate control experiments with which to compare results obtained in test assays.

Performance of an assay method according to the present invention may be followed by isolation and/or manufacture and/or use of a compound, substance or molecule which tests positive for ability to activate E2F2 or a mediated activity, for example effect on ECE-1b promoter. Following identification of a suitable agent it may be investigated further. Furthermore, it may be manufactured and/or used in preparation, i.e. manufacture or formulation, of a composition such as a medicament, pharmaceutical composition or drug. These may be administered to individuals.

The amount of test substance or compound which may be added to an assay of the invention will normally be determined by trial and error depending upon the type of compound used. Typically, from about 0.001 nM to 1 mM or more concentrations of putative activator compound may be used, for example from 0.01 nM to 100 .mu.M, e.g. 0.1 to 50 μM, such as about 10 μM. Greater concentrations may be used when a peptide is the test substance. Even a molecule which has a weak effect may be a useful lead compound for further investigation and development.

Compounds which may be used may be natural or synthetic chemical compounds used in drug screening programs. Extracts of plants which contain several characterized or uncharacterized components may also be used.

A compound found to have the ability to act as an E2F2 activator has therapeutic and other potential in a number of contexts, as discussed. For therapeutic treatment such a compound may be used in combination with any other active substance, e.g. to treat hypertension, or to treat a cardiac condition.

Thus, an agent identified using one or more primary screens (e.g. in a cell-free system) as having ability to activate E2F2 may be assessed further using one or more secondary screens.

Pharmaceutical Compositions

The present invention features pharmaceutical preparations comprising an effective amount of an E2F2 polypeptide or an E2F2 activator. In one embodiment, the invention provides an E2F2 fusion protein (e.g., at least a portion of E2F2 and a protein transduction domain), together with pharmaceutically acceptable carriers, where the compounds provide for the treatment of hypertension, pulmonary hypertension, or virtually any cardiac indication. Pharmaceutical preparations of the invention have both therapeutic and prophylactic applications.

Hypertension treated by the methods of the invention can be, for example, pulmonary hypertension. The cardiac condition treated by the methods of the invention can be, for example, heart failure. According to certain preferred embodiments, hypertension can be associated with a cardiovascular condition selected from the group consisting of cardiac hypertrophy, reduced systolic function, reduced diastolic function, maladaptive hypertrophy, heart failure with preserved systolic function, diastolic heart failure, hypertensive heart disease, aortic and mitral valve disease, pulmonary valve disease, hypertrophic cardiomyopathy, hypertrophic cardiomyopathy, post ischemic and post-infarction cardiac remodeling and cardiac failure.

The compositions should be sterile and contain a therapeutically effective amount of an E2F2 polypeptide in a unit of weight or volume suitable for administration to a subject (e.g., a human patient). The compositions and combinations of the invention can be part of a pharmaceutical pack, where the E2F2 polypeptide is present in individual dosage amounts.

Pharmaceutical compositions of the invention to be used for prophylactic or therapeutic administration should be sterile. Sterility is readily accomplished by filtration through sterile filtration membranes (e.g., 0.2 μm membranes), by gamma irradiation, or any other suitable means known to those skilled in the art. Therapeutic compositions generally are placed into a container having a sterile access port, for example, an intravenous solution bag or vial having a stopper pierceable by a hypodermic injection needle. These compositions ordinarily will be stored in unit or multi-dose containers, for example, sealed ampoules or vials, as an aqueous solution or as a lyophilized formulation for reconstitution.

Whether it is a polypeptide, antibody, peptide, nucleic acid molecule, small molecule, mimetic or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of the condition being treated. Prescription of treatment, e.g. decisions on dosage etc, is within the responsibility of general practitioners and other medical doctors. In preferred embodiments of the invention, the agent is an E2F2 fusion polypeptide. In exemplary embodiments, the fusion protein comprises at least a fragment of an E2F2 polypeptide and a protein transduction domain.

A composition may be administered alone or in combination with other treatments, either simultaneously or sequentially dependent upon the condition to be treated. For example, in certain embodiments, the condition to be treated is hypertension. A composition of the invention may be administered alone, or alternatively in combination with other known agents that treat hypertension, for example ACE inhibitors, angiotensin II receptor blockers, diuretics, calcium antagonists, direct vasodilators, adrenergic inhibitors. Likewise, in another particular embodiment the condition to be treated is a cardiac condition. Thus, a composition of the invention may be administered alone, or alternatively in combination with other known agents that treat a cardiac condition.

Pharmaceutical compositions according to the present invention, and for use in accordance with the present invention, may include, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

In one embodiment, a pharmaceutical composition includes an effective amount of an E2F2 activator. The compositions should be sterile and contain a therapeutically effective amount of an E2F2 activator in a unit of weight or volume suitable for administration to a subject (e.g., a human patient). The compositions and combinations of the invention can be part of a pharmaceutical pack, where the E2F2 activator is present in individual dosage amounts.

Pharmaceutical compositions of the invention to be used for prophylactic or therapeutic administration should be sterile. Sterility is readily accomplished by filtration through sterile filtration membranes (e.g., 0.2 μm membranes), by gamma irradiation, or any other suitable means known to those skilled in the art. Therapeutic compositions generally are placed into a container having a sterile access port, for example, an intravenous solution bag or vial having a stopper pierceable by a hypodermic injection needle. These compositions ordinarily will be stored in unit or multi-dose containers, for example, sealed ampoules or vials, as an aqueous solution or as a lyophilized formulation for reconstitution.

An E2F2 activator may be combined, optionally, with a pharmaceutically acceptable excipient. The term "pharmaceutically-acceptable excipient" as used herein means one or more compatible solid or liquid filler, diluents or encapsulating substances that are suitable for administration into a human. The term "carrier" denotes an organic or inorganic ingredient, natural or synthetic, with which the active ingredient is combined to facilitate administration. The components of the pharmaceutical compositions also are capable of being co-mingled with an E2F2 activator of the present invention, and with each other, in a manner such that there is no interaction that would substantially impair the desired pharmaceutical efficacy.

Compounds of the present invention can be contained in a pharmaceutically acceptable excipient. The excipient preferably contains minor amounts of additives such as substances that enhance isotonicity and chemical stability. Such materials are non-toxic to recipients at the dosages and concentrations employed, and include buffers such as phosphate, citrate, succinate, acetate, lactate, tartrate, and other organic acids or their salts; tris-hydroxymethylaminomethane (TRIS), bicarbonate, carbonate, and other organic bases and their salts; antioxidants, such as ascorbic acid; low molecular weight (for example, less than about ten residues) polypeptides, e.g., polyarginine, polylysine, polyglutamate and polyaspartate; proteins, such as serum albumin, gelatin, or immunoglobulins; hydrophilic polymers, such as polyvinylpyrrolidone (PVP), polypropylene glycols (PPGs), and polyethylene glycols (PEGs); amino acids, such as glycine, glutamic acid, aspartic acid, histidine, lysine, or arginine; monosaccharides, disaccharides, and other carbohydrates including cellulose or its derivatives, glucose, mannose, sucrose, dextrins or sulfated carbohydrate derivatives, such as heparin, chondroitin sulfate or dextran sulfate; polyvalent metal ions, such as divalent metal ions including calcium ions, magnesium ions and manganese ions; chelating agents, such as ethylenediamine tetraacetic acid (EDTA); sugar alcohols, such as mannitol or sorbitol; counterions, such as sodium or ammonium; and/or nonionic surfactants, such as polysorbates or poloxamers. Other additives may be included, such as stabilizers, anti-microbials, inert gases, fluid and nutrient replenishers (i.e., Ringer's dextrose), electrolyte replenishers, and the like, which can be present in conventional amounts.

The compositions, as described above, can be administered in effective amounts. The effective amount will depend upon the mode of administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject having a cardiac disease or disorder associated with hypertrophic morphological, cellular, or molecular remodeling, an effective amount is sufficient to prevent, reduce, stabilize, or reverse an alteration associated with cardiac hypertrophy. With respect to a subject having a cardiac disease or disorder, an effective amount is an amount sufficient to stabilize, slow, or reduce a symptom associated with the cardiac condition. Generally, doses of the compounds of the present invention would be from about 0.01 mg/kg per day to about 1000 mg/kg per day. In one embodiment, 25, 50, 75, 100, 125, 150 or 200 mg of a E2F2 activator is administered to a subject. Preferably, 100 mg of a E2F2 activator is administered. Desirably, the E2F2 activator inhibitor is administered in an amount sufficient to achieve a peak concentration of 10, 25, 50, 75, or 100 nM in plasma. Preferably, the peak concentration is 50 nM. Effective doses range from 0.1 nM to 200 nM, where the bottom of the range is any integer between 1 and 199, and the top of the range is any integer between 2 and 200. Desirably, an effective dose results in a free plasma an E2F2 activator concentration ranging from 10-50 nM; but it can be as much as 200 nM or as low as 1-2 nM. Exemplary concentrations include 0.1, 1, 5, 10, 20, 25, 30, 40, or 50 nM. It is expected that doses ranging from about 5 to about 2000 mg/kg will be. Lower doses will result from certain forms of administration, such as intravenous administration and pharmaceutical. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of a composition of the present invention.

A variety of administration routes are available. The methods of the invention, generally speaking, may be practiced using any mode of administration that is medically acceptable, meaning any mode that produces effective levels of the active compounds without causing clinically unacceptable adverse effects. In one preferred embodiment, a composition of the invention is administered orally. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule.

Pharmaceutical compositions of the invention can comprise one or more pH buffering compounds to maintain the pH of the formulation at a predetermined level that reflects physiological pH, such as in the range of about 5.0 to about 8.0. The pH buffering compound used in the aqueous liquid formulation can be an amino acid or mixture of amino acids, such as histidine or a mixture of amino acids such as histidine and glycine. Alternatively, the pH buffering compound is preferably an agent which maintains the pH of the formulation at a predetermined level, such as in the range of about 5.0 to about 8.0, and which does not chelate calcium ions. Illustrative examples of such pH buffering compounds include, but are not limited to, imidazole and acetate ions. The pH buffering compound may be present in any amount suitable to maintain the pH of the formulation at a predetermined level.

Pharmaceutical compositions of the invention can also contain one or more osmotic modulating agents, i.e., a compound that modulates the osmotic properties (e.g, tonicity, osmolality and/or osmotic pressure) of the formulation to a level that is acceptable to the blood stream and blood cells of recipient individuals. The osmotic modulating agent can be an agent that does not chelate calcium ions. The osmotic modulating agent can be any compound known or available to those skilled in the art that modulates the osmotic properties of the formulation. One skilled in the art may empirically determine the suitability of a given osmotic modulating agent for use in the inventive formulation. Illustrative examples of suitable types of osmotic modulating agents include, but are not limited to: salts, such as sodium chloride and sodium acetate; sugars, such as sucrose, dextrose, and mannitol; amino acids, such as glycine; and mixtures of one or more of these agents and/or types of agents. The osmotic modulating agent(s) may be present in any concentration sufficient to modulate the osmotic properties of the formulation.

Compositions comprising a compound of the present invention can contain multivalent metal ions, such as calcium ions, magnesium ions and/or manganese ions. Any multivalent metal ion that helps stabilizes the composition and that will not adversely affect recipient individuals may be used. The skilled artisan, based on these two criteria, can determine suitable metal ions empirically and suitable sources of such metal ions are known, and include inorganic and organic salts.

Pharmaceutical compositions of the invention can also be a non-aqueous liquid formulation. Any suitable non-aqueous liquid may be employed, provided that it provides stability to the active agents (s) contained therein. Preferably, the non-aqueous liquid is a hydrophilic liquid. Illustrative examples of suitable non-aqueous liquids include: glycerol; dimethyl sulfoxide (DMSO); polydimethylsiloxane (PMS); ethylene glycols, such as ethylene glycol, diethylene glycol, triethylene glycol, polyethylene glycol ("PEG") 200, PEG 300, and PEG 400; and propylene glycols, such as dipropylene glycol, tripropylene glycol, polypropylene glycol ("PPG") 425, PPG 725, PPG 1000, PPG 2000, PPG 3000 and PPG 4000.

Pharmaceutical compositions of the invention can also be a mixed aqueous/non-aqueous liquid formulation. Any suitable non-aqueous liquid formulation, such as those described above, can be employed along with any aqueous liquid formulation, such as those described above, provided that the mixed aqueous/non-aqueous liquid formulation provides stability to the compound contained therein. Preferably, the non-aqueous liquid in such a formulation is a hydrophilic liquid. Illustrative examples of suitable non-aqueous liquids include: glycerol; DMSO; PMS; ethylene glycols, such as PEG 200, PEG 300, and PEG 400; and propylene glycols, such as PPG 425, PPG 725, PPG 1000, PPG 2000, PPG 3000 and PPG 4000.

Suitable stable formulations can permit storage of the active agents in a frozen or an unfrozen liquid state. Stable liquid formulations can be stored at a temperature of at least $-70°$ C., but can also be stored at higher temperatures of at least $0°$ C., or between about $0.1°$ C. and about $42°$ C., depending on the properties of the composition. It is generally known to the skilled artisan that proteins and polypeptides are sensitive to changes in pH, temperature, and a multiplicity of other factors that may affect therapeutic efficacy.

Other delivery systems can include time-release, delayed release or sustained release delivery systems. Such systems can avoid repeated administrations of compositions of the invention, increasing convenience to the subject and the physician. Many types of release delivery systems are available and known to those of ordinary skill in the art. They include polymer base systems such as polylactides (U.S. Pat. No. 3,773,919; European Patent No. 58,481), poly(lactide-glycolide), copolyoxalates, polycaprolactones, polyesteramides, polyorthoesters, polyhydroxybutyric acids, such as poly-D-(−)-3-hydroxybutyric acid (European Patent No. 133, 988), copolymers of L-glutamic acid and gamma-ethyl-L- glutamate (Sidman, K. R. et al., Biopolymers 22: 547-556), poly (2-hydroxyethyl methacrylate) or ethylene vinyl acetate (Langer, R. et al., J. Biomed. Mater. Res. 15:267-277; Langer, R. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono- di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

Another type of delivery system that can be used with the methods and compositions of the invention is a colloidal dispersion system. Colloidal dispersion systems include lipid-based systems including oil-in-water emulsions, micelles, mixed micelles, and liposomes. Liposomes are artificial membrane vessels, which are useful as a delivery vector in vivo or in vitro. Large unilamellar vessels (LUV), which range in size from 0.2-4.0 µm, can encapsulate large macromolecules within the aqueous interior and be delivered to cells in a biologically active form (Fraley, R., and Papahadjopoulos, D., Trends Biochem. Sci. 6: 77-80).

Liposomes can be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3dioleyloxy)-propyl]-N,N,N-trimethylammonium chloride (DOTMA) and dimethyl dioctadecylammonium bromide (DDAB). Methods for making liposomes are well known in the art and have been described in many publications, for example, in DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88, 046; EP 143,949; EP 142,641; Japanese Pat. Appl. 83-118008; U.S. Pat. Nos. 4,485,045 and 4,544,545; and EP 102,324. Liposomes also have been reviewed by Gregoriadis, G., Trends Biotechnol., 3: 235-241).

Another type of vehicle is a biocompatible microparticle or implant that is suitable for implantation into a mammalian recipient. Exemplary bioerodible implants that are useful in accordance with this method are described in PCT International application no. PCT/US/03307 (Publication No. WO 95/24929, entitled "Polymeric Gene Delivery System"). PCT/US/0307 describes biocompatible, preferably biodegradable polymeric matrices for containing an exogenous gene under the control of an appropriate promoter. The polymeric matrices can be used to achieve sustained release of the exogenous gene or gene product in the subject.

The polymeric matrix preferably is in the form of a microparticle such as a microsphere (wherein an agent is dispersed throughout a solid polymeric matrix) or a microcapsule (wherein an agent is stored in the core of a polymeric shell). Microcapsules of the foregoing polymers containing drugs are described in, for example, U.S. Pat. No. 5,075,109. Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery that is to be used. Preferably, when an aerosol route is used the polymeric matrix and composition are encompassed in a surfactant vehicle. The polymeric matrix composition can be selected to have both favorable degradation rates and also to be formed of a material, which is a bioadhesive, to further increase the effectiveness of transfer. The matrix composition also can be selected not to degrade, but rather to release by diffusion over an extended period of time. The delivery system can also be a biocompatible microsphere that is suitable for local, site-specific delivery. Such microspheres are disclosed in Chickering, D. E., et al., Biotechnol. Bioeng., 52: 96-101; Mathiowitz, E., et al., Nature 386: 410-414.

Both non-biodegradable and biodegradable polymeric matrices can be used to deliver the compositions of the invention to the subject. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly (ortho)esters, poly(butic acid), poly(valeric acid), and poly (lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

The agent (e.g. a small molecule) may be administered in a precursor form, for conversion to the active form by an activating agent produced in, or targeted to, the cells to be treated. This type of approach is sometimes known as ADEPT or VDEPT, the former involving targeting the activator to the cells by conjugation to a cell-specific antibody, while the latter involves producing the activator, e.g. an enzyme, in a vector by expression from encoding DNA in a viral vector (see for example, EP-A-415731 and WO 90/07936).

The agent may be administered in a localized manner to a specific site, or may be delivered in a manner in which it targets a certain cell population. Targeting therapies may be used to deliver the active agent more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Instead of administering these agents directly, they may be produced in the target cells by expression from an encoding gene introduced into the cells, e.g. in a viral vector. The vector may targeted to the specific cells to be treated, or it may contain regulatory elements which are switched on more or less selectively by the target cells.

An agent may be administered in a form which is inactive but which is converted to an active form in the body. For instance, the agent may be phosphorylated (e.g. to improve solubility) with the phosphate being cleaved to provide an active form of the agent in the body.

Nucleic acid according to the present invention, encoding a polypeptide or peptide able to modulate, e.g. agents that increase ECE-1B expression, may be used in methods of gene therapy, for instance in treatment of individuals, e.g. with the aim of preventing or curing (wholly or partially) a disorder, for example a cardiac condition, hypertension, or pulmonary hypertension.

The step of introducing the expression vector into the selected target cell or tissue will differ depending on the intended use and species, and can involve one or more of non-viral and viral vectors, cationic liposomes, retroviruses, and adenoviruses such as, for example, described in Mulligan, R. C., (1993). Such methods can include, for example:

Local application of the expression vector by injection (Wolff et al., 1990), surgical implantation, instillation or any other means. This method can also be used in combination with local application by injection, surgical implantation, instillation or any other means, of cells responsive to the protein encoded by the expression vector so as to increase the effectiveness of that treatment. This method can also be used in combination with local application by injection, surgical implantation, instillation or any other means, of another factor or factors required for the activity of the protein.

General systemic delivery by injection of DNA, (Calabretta et al., 1993), or RNA, alone or in combination with liposomes (Zhu et al., 1993), viral capsids or nanoparticles (Bertling et al., 1991) or any other mediator of delivery. Improved targeting might be achieved by linking the polynucleotide/expression vector to a targeting molecule (the so-called "magic bullet" approach employing, for example, an antigen-binding molecule), or by local application by injection, surgical implantation or any other means, of another factor or factors required for the activity of the protein encoded by the expression vector, or of cells responsive to the protein. For example, in the case of a liposome containing E2F2 polynucleotides, the liposome may be targeted to specific cells by the incorporation of immuno-interactive agents into the liposome coat which are specific for the cell of interest, e.g. contains those cell-specific cell surface antigens.

Injection or implantation or delivery by any means, of cells that have been modified ex vivo by transfection (for example, in the presence of calcium phosphate: Chen et al., 1987, or of cationic lipids and polyamines: Rose et al., 1991), infection, injection, electroporation (Shigekawa et al., 1988) or any other way so as to increase the expression of the polynucleotide in those cells. The modification can be mediated by plasmid, bacteriophage, cosmid, viral (such as adenoviral or retroviral; Mulligan, 1993; Miller, 1992; Salmons et al., 1993) or other vectors, or other agents of modification such as liposomes (Zhu et al., 1993), viral capsids or nanoparticles (Bertling et al., 1991), or any other mediator of modification. The use of cells as a delivery vehicle for genes or gene products has been described by Barr et al., 1991 and by Dhawan et al., 1991. Treated cells can be delivered in combination with any nutrient, growth factor, matrix or other agent that will promote their survival in the treated subject.

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

Combination Therapies

Compositions of the invention may, if desired, be delivered in combination with any other polypeptide or polynucleotide therapeutic of the invention, including detectably labeled fusion proteins to assist in monitoring the efficacy of the protein therapy, or with any conventional therapeutic known in the art. In one embodiment, a fusion polypeptide of the invention, such as E2F2 fused to a protein transduction domain, is used to, reduce hypertension, pulmonary hypertension, or a cardiac condition, for example cardiac failure, in a subject. This therapeutic effect is desirable even if the therapeutic method does not entirely eliminate the patient's symptoms or tendency to the disease. Accordingly, fusion polypeptides of the invention may be administered together with a known drug to treat hypertension, pulmonary hypertension, or a cardiac condition such as cardiac failure, to alleviate a symptom or complication associated with any of the conditions. Desirably, a therapeutic fusion polypeptide of the invention reduces hypertension, pulmonary hypertension, or a cardiac condition by at least about 5, 10, or 15%, more desirably by at least about 20%, 25%, or even by 30%, or even more desirably by 50%, 75%, 85% or more. In other embodiments, the polypeptide therapeutic is combined with a polynucleotide of the invention (e.g., a polynucleotide encoding an E2F2 or fusion protein). In other embodiments, compositions of the invention are used in combination with other therapies to treat hypertension, pulmonary hypertension, or a cardiac condition. Combinations of the invention may be formulated together and administered simultaneously or may be administered within twenty-four hours, within 2, 3, or 5 days, or within 1, 2, 3 or 5 weeks of each other.

Kits or Pharmaceutical Systems

The present compositions may be assembled into kits or pharmaceutical systems for use in treating hypertension, pulmonary hypertension or a cardiac condition. Kits or pharmaceutical systems according to this aspect of the invention comprise a carrier means, such as a box, carton, tube or the like, having in close confinement therein one or more container means, such as vials, tubes, ampoules, bottles and the like. The kits or pharmaceutical systems of the invention may also comprise associated instructions for using the agents of the invention.

If desired compositions of the invention or combinations thereof are provided together with instructions for administering them to a subject having or at risk of developing a cardiac condition associated with hypertrophy. The instructions will generally include information about the use of the compounds for the treatment or prevention of hypertension, pulmonary hypertension or a cardiac condition. In other embodiments, the instructions include at least one of the following: description of the compound or combination of compounds; dosage schedule and administration for treatment of a cardiac condition or symptoms thereof; precautions; warnings; indications; counter-indications; over dosage information; adverse reactions; animal pharmacology; clinical studies; and/or references. The instructions may be printed directly on the container (when present), or as a label applied to the container, or as a separate sheet, pamphlet, card, or folder supplied in or with the container.

Provided by the invention are pharmaceutical systems comprising a composition comprising an E2F2 activator in a pharmaceutically acceptable excipient, wherein the pharmaceutical system is labeled for use in the treatment or prevention of a hypertension. Hypertension can be, for example, pulmonary hypertension. Hypertension can be associated with a cardiovascular condition, such as, but not limited to cardiac failure.

Also provided by the invention are pharmaceutical systems comprising a composition comprising an E2F2 activator in a pharmaceutically acceptable excipient, wherein the pharmaceutical system is labeled for use in the treatment or prevention of a cardiac condition. The cardiac condition can be, but is not limited to, cardiac failure, cardiac hypertrophy, reduced systolic function, reduced diastolic function, maladaptive hypertrophy, heart failure with preserved systolic function, diastolic heart failure, hypertensive heart disease, aortic stenosis, hypertrophic cardiomyopathy, and post ischemic cardiac remodeling. In particular cases, cardiac failure can occur independent of hypertension.

Also provided are pharmaceutical systems comprising a composition comprising an E2F2 activator in a pharmaceutically acceptable excipient, wherein the pharmaceutical system is labeled for use in the enhancement of cardiac function. In any of the pharmaceutical systems of the invention, the E2F2 activator can be provided in a sustained release formulation. Further, the composition provided in the pharmaceutical system, in some embodiments, consists essentially of an E2F2 activator.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are provided to illustrate the invention, not to limit it. Those skilled in the art will understand that the specific constructions provided below may be changed in numerous ways, consistent with the above described invention while retaining the critical properties of the compounds or combinations thereof.

EXAMPLES

Example 1

Mice Deficient in E2F2 are Hypertensive

In this experiment, the arterial blood pressure (BP) of E2F2-null mice at 6 months of age was measured by the tail cuff method. Arterial BP was found to be significantly higher in E2F2-null mice (102.2+4.02 mmHg), compared to that of wild-type (WT) littermates (91.8+2.81 mmHg) (n=16, P<0.05), as shown in FIG. 1.

Example 2

E2F2 Regulates Vessel Contractility ex vivo

Figure 2A:
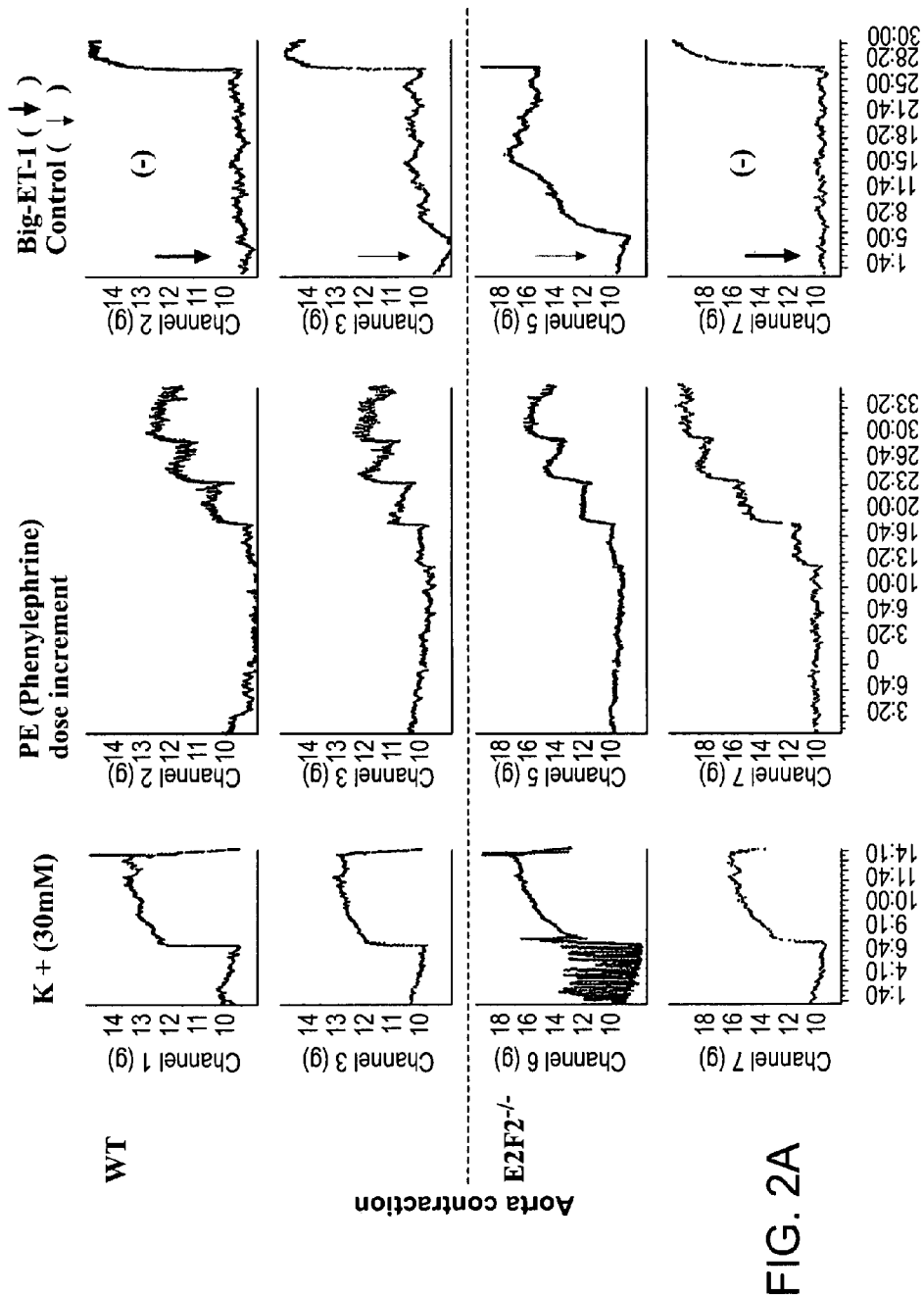
FIGS. 2A and 2B are graphs showing that E2F2 regulates vessel contractility ex vivo.
Figure 2B:
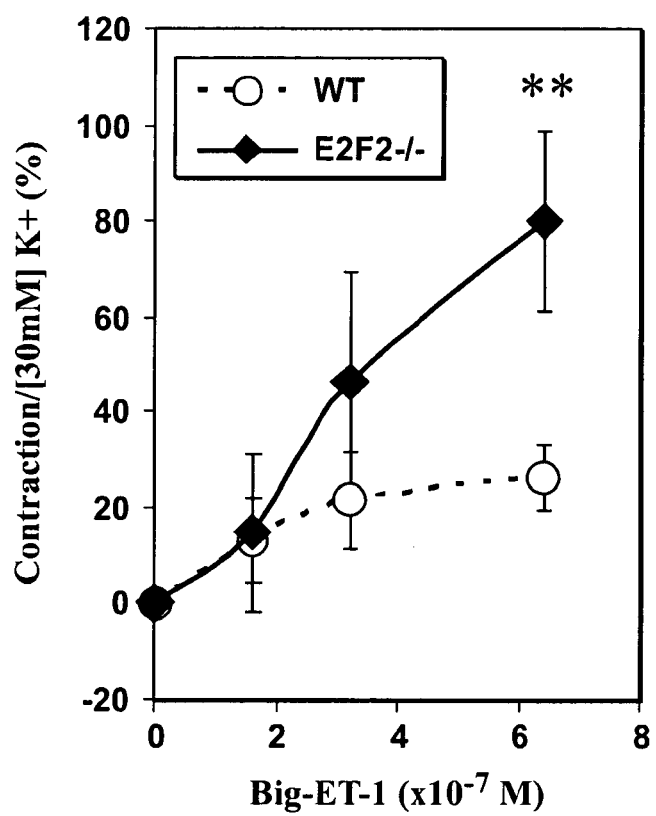

The effect of E2F2 on vessel contractility ex vivo was examined. Aortic ring assay was performed using endothelial-intact aortas isolated from E2F2-null mice and WT littermates to assess the ECE-1 bioactivity. While KCL (30 mM)- or Phenylephrine ($10^{-9}$-$3\times10^{-6}$M)-induced contraction and Acetylcholine ($10^{-9}$-$10^{-6}$M)-induced relaxation were similar between the two groups, the E2F2-null aortas demonstrated a significantly increased contractile response to big Endothelin-1 (ET-1) ($2.7\times10^{-7}$ M to $2.1\times10^6$ M). At maximum, E2F2-null aorta contracted to 80.0+18.81 vs. 26.5+6.77 by WT aorta (% Contraction/KCl, n=4, P<0.05). These results indicated a specific increase in ECE-1 activity due to the loss of E2F2. FIG. 2A shows representative records of the aortic ring assay. FIG. 2B shows the quantification of contraction (expressed as percent against [30 mM] $K^+$ treatment).

Together, these results indicated that the effect of E2F2 on vessel contractility ex vivo is likely to be dependent on Endothelin Converting Enzyme-1 (ECE-1) activity. Loss of E2F2 in the aortic artery leas to a hyper-contractility in response to ECE-1 substrate, big Endothelin-1 (ET-1). This novel function is specific to E2F2, and is independent of its cell cycle regulation.

Example 3

E2F2 Positively Regulates ECE-1b Promoter Activity in Cultured ECs

Figure 3A:
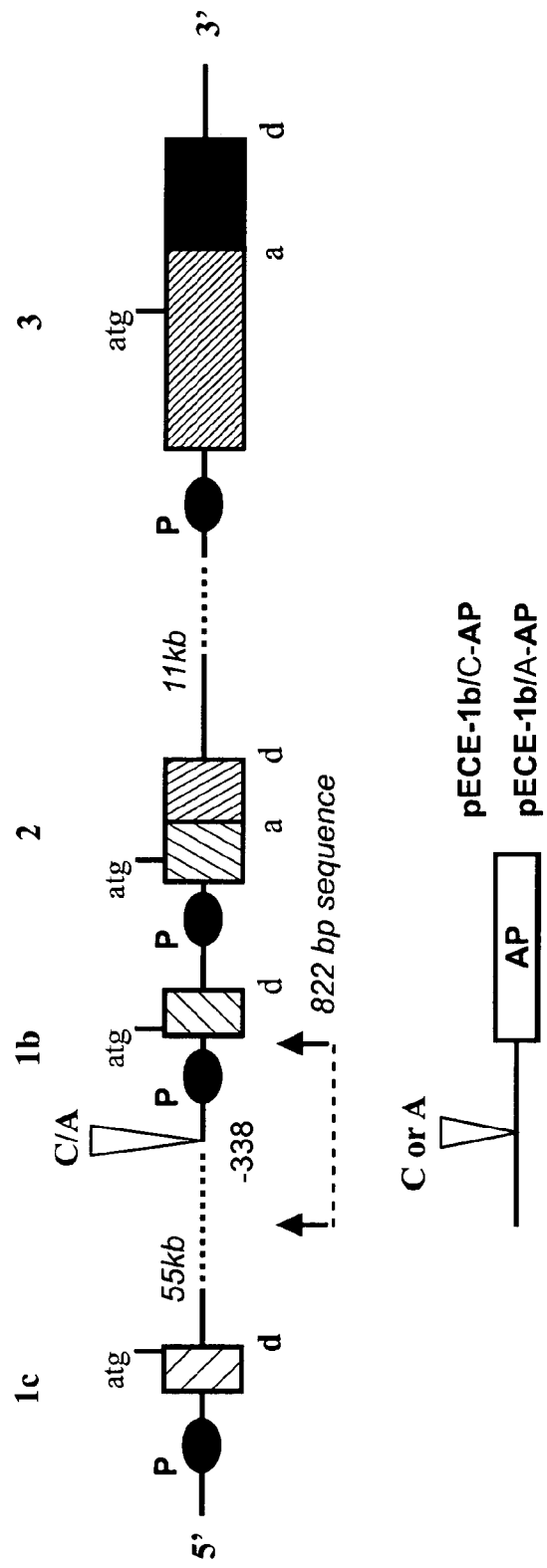
FIGS. 3A to 3D show that E2F2 positively regulates ECE-1b promoter activity in cultured endothelial cells (Ecs).
Figure 3B:
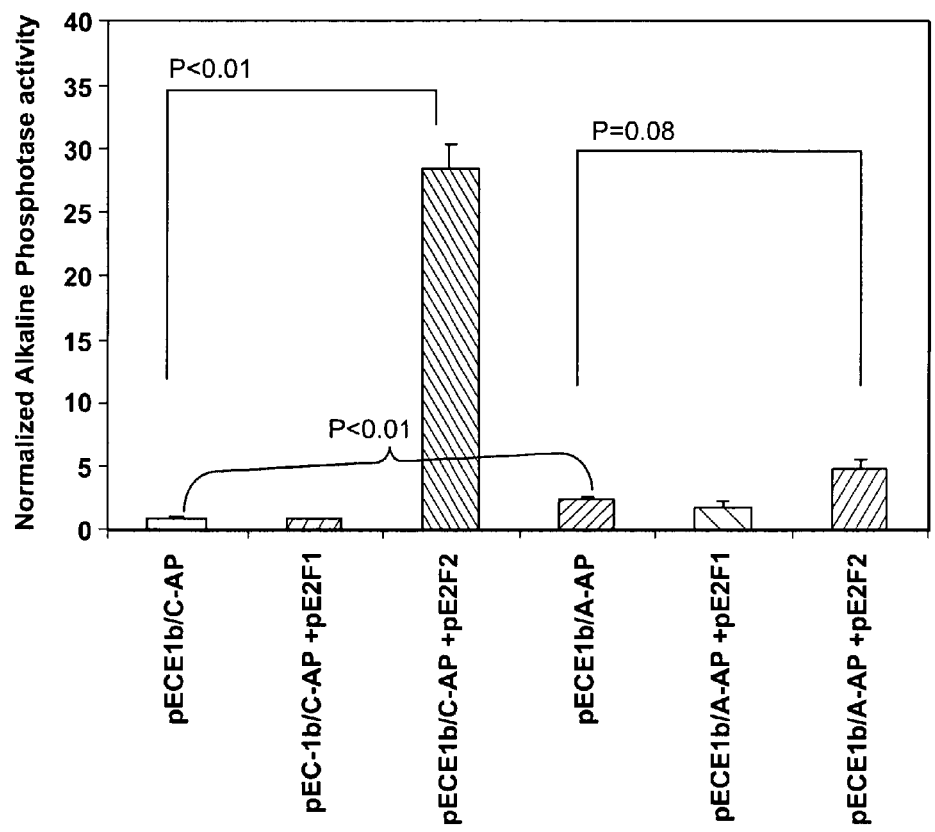
Figure 3C:
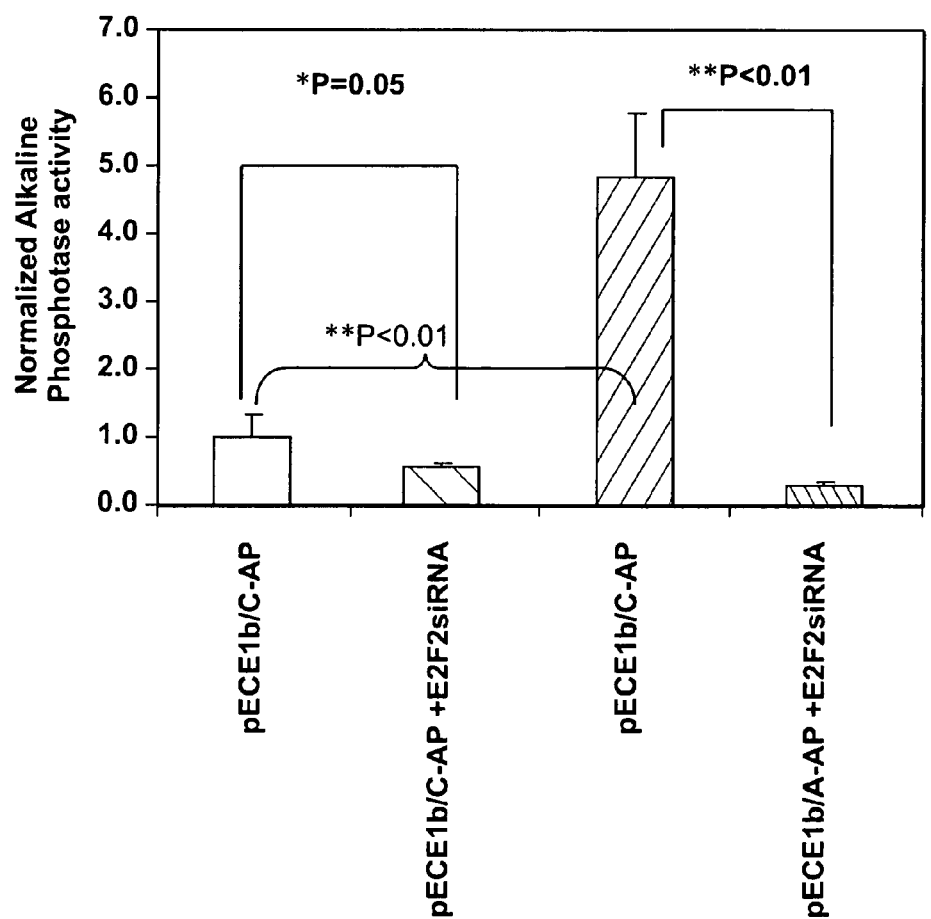
Figure 3D:
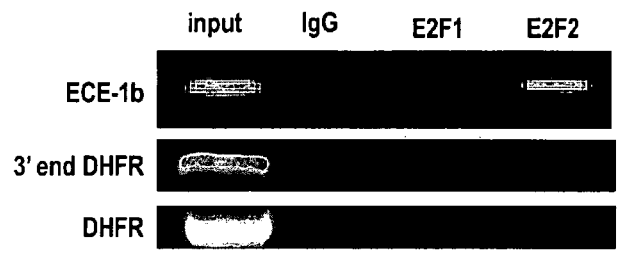

Next, to determine whether the increased ECE-1 activity in E2F2-null mice is due to a specific regulation of ECE-1b promoter by E2F2, bovine aortic endothelial cells (BAEC) were co-transfected with human E2F2 plasmid (pE2F2) and human ECE-1b promoter plasmids (pECE1b/C[orA]-AP), as shown in FIG. 3A. An alkaline Phosphotase (AP) reporter assay was performed. Overexpression of E2F2 significantly increased the native form, but not the (C-338A) polymorphic form, of ECE-1b promoter activity (28.7 vs. 1.9 fold induction, $P<0.001$) (FIG. 3B). This data indicated that E2F2 activated ECE-1b and that the C-338A polymorphism may blunt E2F2-induced ECE-1b expression to increase ECE-1 bioactivity. This result is further confirmed by siRNA-mediated endogenous E2F2 gene knockdown, where the activity of the (C-338A) polymorphic form of the ECE-1b promoter was significantly attenuated while the native form promoter activity was reduced to lesser extent (FIG. 3C). Moreover, chromatin immunoprecipitation was performed, which demonstrated that endogenous E2F2 occupies ECE-1b promoter region in vivo, confirming a direct regulation of ECE-1b transcription by endogenous E2F2 (FIG. 3D).

Example 4

Knockdown of Endogenous E2F2 in Bovine Endothelial Cells Leads to a Derease in the Level of Intracellular Endosomal/Lysosomal ECE-1 (ECE-1b) but an Increase in the Level of Plasma Membrane ECE-1 (ECE-1a/c/d)

Figure 4A:
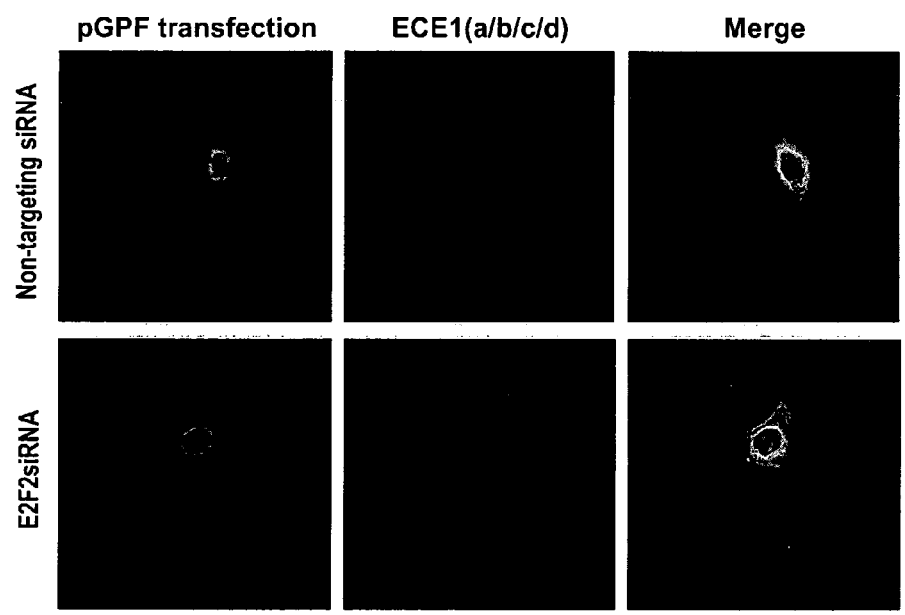
FIG. 4A is a panel of immunoflourescent images showing that knockdown of endogenous E2F2 in bovine endothelial cells (BAEC) leads, to a reduction in peri-nuclear endosomal ECE-1 isoform (ECE-1b) and an increase in plasma membrane ECE-1 isoforms (ECE-1 a/c). siRNA transfected cells were co-transfected with GFP-expressing plasmid (pGFP) for labeling, shown in the first (left) set of panels. The immunofluorescent stainings were performed using a Rhodamine-conjugated antibody (second, center panels) that recognizes an epitope shared by ECE-1 a/b/c/d all isoforms.
Figure 4B:
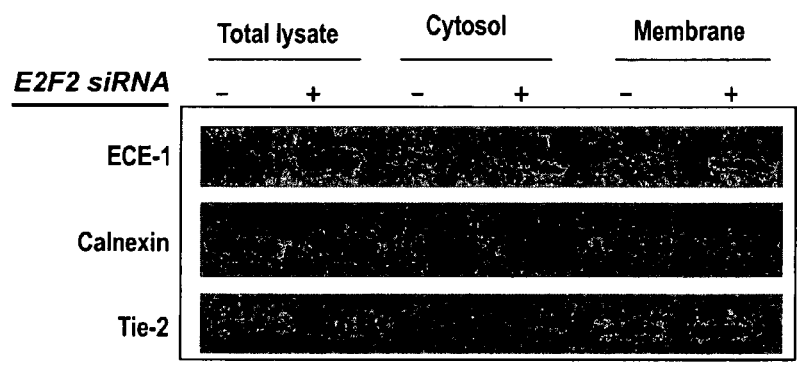
FIG. 4B shows a Western blot analysis following E2F2 siRNA treatment

Knockdown of endogenous E2F2 in bovine endothelial cells (BAEC) lead to a reduction in peri-nuclear endosomal ECE-1 isoform (ECE-1b) and an increase in plasma membrane ECE-1 isforms (ECE-1a/c). The siRNA transfected cells were co-transfected with GFP-expressing plasmid (pGFP) for immunoflouresncent labeling, as shown om FIG. 4A. The immunofluorescent stainings were performed using a Rhodamine-conjugated antibody (second, center panels) that recognized an epitope shared by ECE-1 a/b/c/d all isoforms. Therefore, loss or knockdown of E2F2 leads to unbalanced ratio of [Endosomal ECE-1b]/[Cytoplasmic membrane ECE-1a, c)]. The increased ECE-1a/c protein activity may confer big ET-mediated vessel hyper-contractility. To further differentiate between the plasma membrane and intracellular isoforms, the surface of HUVECs in culture were labeled with non-permeable Sulfo-NHS-SS-Biotin. The plasma membrane proteins vs. cytosolic proteins were fractionated, and subjected to Western blot analysis. As shown in FIG. 4B, E2F2 siRNA treatment resulted in a significantly reduced ECE-1 immunoactivity in the cytosol fraction and interestingly, a significant increase in ECE-1 immunoactivity in the plasma membrane fraction (FIG. 4B). This data was in agreement with the discovery of increased bioactivity of ECE-1 on the cell surface of $E2F2^{-/-}$ vessels as demonstrated by the increased contractility of $E2F2^{-/-}$ aortic vessels in response to big ET-1 (FIG. 2). Without wishing to be bound by theory, it is likely that intracellular ECE-1b acts as a negative modulator of other membrane ECE-1a/c/d levels and activities. Therefore, these data establish the concept that loss or knockdown of E2F2, via down-regulation of late endosomal ECE-1b isoform expression, indirectly leads to an increase in ECE-1a/c/d isoform protein activity and ET-1-mediated vessel hypercontractility and hypertension.

Figure 5:
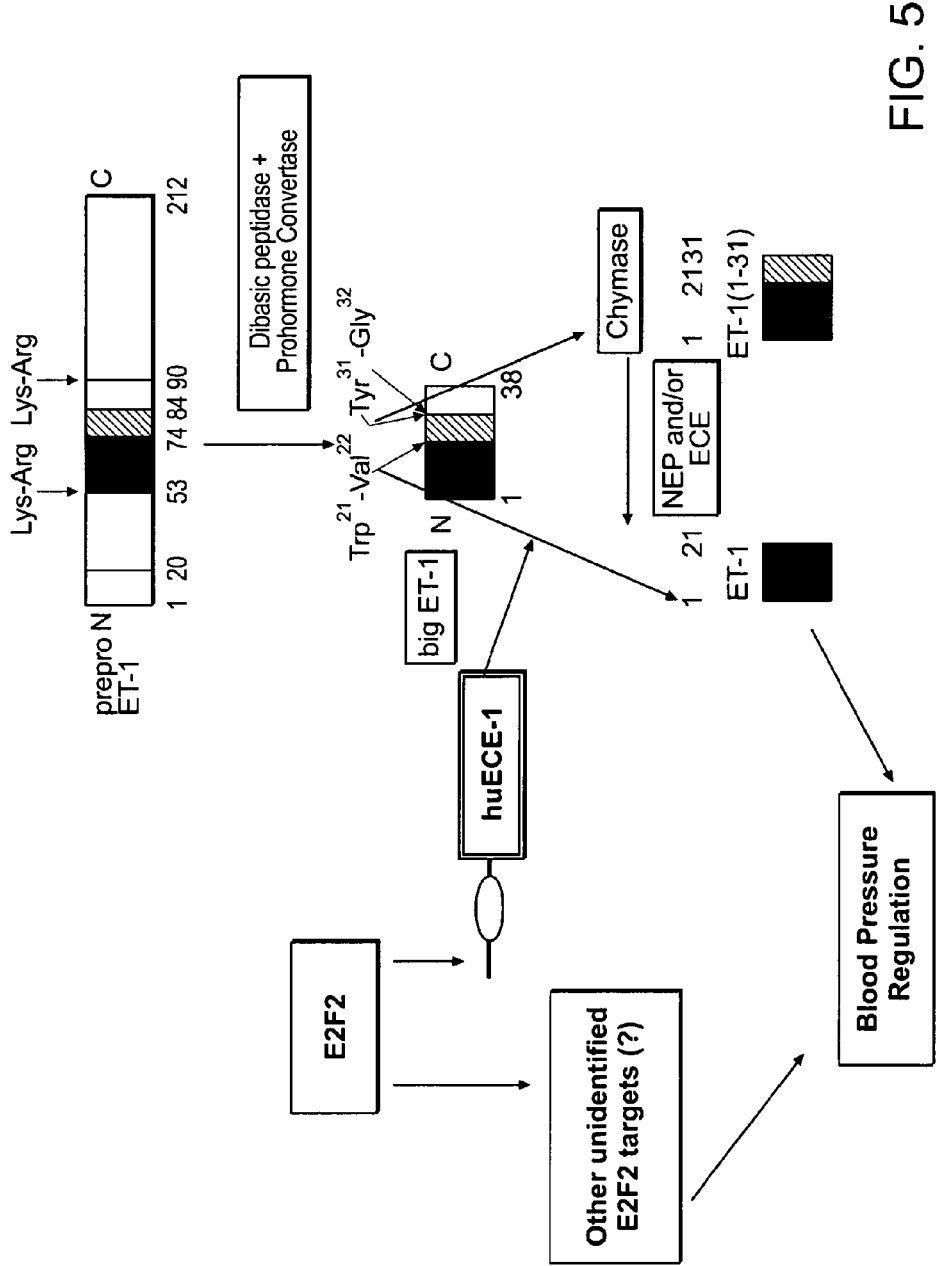
FIG. 5 is a schematic diagram that provides a model for E2F2 activity.

FIG. 5 is a schematic diagram that provides a model for E2F2 activity. The diagram provides a brief schema describing how E2F2 might regulate blood pressure.

Taken together, the data presented provides genetic evidence that: 1) E2F2 regulates blood pressure. The data indicates that deregulated E2F2 activity contributes to the pathogenesis of hypertension and treatment with E2F2 likely lowers blood pressure; 2) E2F2 regulates ECE-1b expression and ECE-1-dependent vessel contractility; 3) modulation of the specific expression of ECE-1b may also provide an alternative therapy for human hypertension.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for ameliorating hypertension in a subject in need thereof, the method comprising;
    (a) transforming an endothelial cell in vitro with an expression vector comprising a nucleic acid molecule encoding an E2F2 polypeptide fused to a protein transduction domain, wherein the protein transduction domain is selected from the group consisting of an HIV-TAT protein, a unidecapeptide protein transduction domain (YGRKKRRQRRR (SEQ ID NO: 2)), a polyarginine sequence, a VP22 domain, and a antennapedia protein transduction domain, wherein the E2F2 fusion polypeptide retains E2F2 activity;
    (b) expressing the E2F2 polypeptide in the endothelial cell;
    (c) isolating the E2F2 polypeptide; and
    (d) administering the E2F2 polypeptide to the subject, thereby ameliorating the hypertension.

2. The method of claim 1, wherein the endothelial cell in vitro is obtained from the subject.

3. A method for ameliorating hypertension in a subject in need thereof, the method comprising;
    (a) transforming an endothelial cell in vitro with an expression vector comprising a nucleic acid molecule encoding an E2F2 polypeptide fused to a protein transduction domain selected from the group consisting of an HIV-TAT protein, a unidecapeptide protein transduction domain (YGRKKRRQRRR (SEQ ID NO: 2)), a polyarginine sequence, a VP22 domain, and a antennapedia protein transduction domain, wherein the E2F2 fusion polypeptide retains E2F2 activity;
    (b) expressing the E2F2 fusion polypeptide in the endothelial cell; and
    (c) administering the endothelial cell expressing the E2F2 fusion polypeptide to the subject, thereby ameliorating the hypertension.

4. The method of claim 3, wherein the endothelial cell is a human cell.

5. The method of claim 3, wherein the endothelial cell is a cardiac cell.

6. The method of claim 3, wherein the endothelial cell in vitro is obtained from the subject.

7. A method of reducing hypertension in a subject in need thereof, the method comprising:
    administering an effective amount of an E2F2 polypeptide having E2F2 activity to endothelial cells of the subject or
    administering an effective amount of an E2F2 polypeptide fused to a protein transduction domain selected from the group consisting of an HIV-TAT protein, a unidecapeptide protein transduction domain (YGRKKRRQRRR (SEQ ID NO: 2)), a polyarginine sequence, a VP22 domain, and a antennapedia protein transduction domain to endothelial cells of the subject, wherein the E2F2 polypeptide fused to the protein transduction domain retains E2F2 activity.

8. The method of claim 7, wherein the E2F2 activity of the E2F2 polypeptide or of the E2F2 polypeptide fused to the protein transduction domain activates an endothelial converting enzyme 1b (ECE-1b) promoter.

9. The method of claim 7, wherein the hypertension is associated with a cardiovascular condition selected from the group consisting of cardiac hypertrophy, reduced systolic function, reduced diastolic function, maladaptive hypertrophy, heart failure with preserved systolic function, diastolic heart failure, hypertensive heart disease, aortic and mitral valve disease, pulmonary valve disease, hypertrophic cardiomyopathy, hypertrophic cardiomyopathy, post ischemic and post-infarction cardiac remodeling and cardiac failure.

10. The method of claim 7, further comprising the step of measuring relaxation rate, cardiac contractility, cardiac ejection volume, or end-systolic volume, wherein a change in relaxation rate, cardiac contractility, cardiac ejection volume, or end-systolic volume is indicative of reducing hypertension.

11. The method of claim 7, wherein the E2F2 polypeptide fused to the protein transduction domain is an E2F2 polypeptide fused to HIV-TAT protein that possesses E2F2 activity that activates an endothelial converting enzyme 1b (ECE-1b) promoter.

* * * * *